United States Patent
Salb

[11] Patent Number: 5,198,977
[45] Date of Patent: Mar. 30, 1993

[54] SYSTEM AND METHOD FOR LOCALIZATION OF FUNCTIONAL ACTIVITY IN THE HUMAN BRAIN

[76] Inventor: Jesse Salb, 10445 Wilshire Blvd., Los Angeles, Calif. 90024

[21] Appl. No.: 619,187

[22] Filed: Nov. 27, 1990

[51] Int. Cl.$^5$ .............................................. G06F 15/00
[52] U.S. Cl. ............................... 364/413.01; 128/633; 382/6; 356/40
[58] Field of Search ........................ 364/413.01; 382/6; 436/805; 356/39, 40, 445, 448; 422/82.05; 128/633

[56] References Cited

U.S. PATENT DOCUMENTS

| | | | |
|---|---|---|---|
| 3,890,959 | 6/1975 | Youdin et al. | 128/654 |
| 3,994,585 | 11/1976 | Frey | 356/40 |
| 4,223,680 | 9/1980 | Jöbsis | 128/633 |
| 4,281,645 | 8/1981 | Jöbsis | 128/633 |
| 4,357,105 | 11/1982 | Lorentz | 356/40 |
| 4,736,307 | 4/1988 | Salb | 364/413.05 |
| 4,997,769 | 3/1991 | Lundsgaard | 436/33 |

OTHER PUBLICATIONS

Kinuta et al. (1987) Reflectance spectrophotometric measurement of an in vivo local oxygen consumption in the cerebral cortex, J. Cereb Blood Flow Metab. 7:592–598.

Grinvald et al. (1986) Functional architecture of cortex revealed by optical imaging of intrinsic signals, Nature 324:361–364.

Eke A (1982) Reflectometric mapping of microregional blood flow and blood volume in the brain cortex, J Cereb Blood Flow Metal 2:41–53.

Eke A et al. (1979) Induced hemodilution detected by reflectometry for measuring microregional blood flow and blood volume in cat brain cortex, Am J. Physiol 236:H759–H768.

Schuette et al. (1974) A television fluorometer for monitoring oxidative metabolism in intact tissue, Med Instrum 8:331–333.

Primary Examiner—Roy N. Envall, Jr.
Assistant Examiner—Laura Brutman
Attorney, Agent, or Firm—Blakely, Sokoloff, Taylor & Zafman

[57] ABSTRACT

System and method for the localization of functional activity in the human brain during neurosurgery. The system includes an electronic flash illuminator for illuminating the surface of the exposed portion of the patient's brain, optical bandpass filters for sequentially illuminating the exposed brain surface with monochromatic light of a number of predetermined wavelengths, a positioning mechanism for rapid positioning of the optical filters in the path of illumination, a video camera for acquiring an image of the exposed brain surface during illumination with each wavelength of monochromatic light, a circuit for converting the linear output signal of the video camera into a logarithmic signal in video format, a digitizer and frame storage memory for digitizing the logarithmic video signal to obtain multiple two-dimensional matrices. Each matrix represents the magnitude of light reflected at a particular wavelength from a regular grid of points over the exposed brain surface. The system also includes a video frame arithmetic circuit for computing two-dimensional matrices of regional total hemoglobin concentration utilizing the two-dimensional matrices of reflectance data and for transforming the computed matrices into gray-scale or color-scale maps representing total hemoglobin concentration at the grid of points on the exposed brain surface, and a circuit for displaying, on a high-resolution RGB color video monitor, gray-scale or color-scale maps representing either absolute total hemoglobin concentration over the exposed brain surface at a single point in time or the difference between total hemoglobin concentration on the exposed brain surface before and after functional activation of the brain. Functional activation of the brain is accomplished by applying a sensory stimulus to the patient or by having the patient perform a cognitive task in a neuropsychological paradigm appropriately modified for the neurosurgical setting.

18 Claims, 4 Drawing Sheets

SYSTEM AND METHOD FOR LOCALIZATION OF FUNCTIONAL ACTIVITY IN THE HUMAN BRAIN

BACKGROUND OF THE INVENTION

This invention relates to neurosurgery in general, and in particular to a method and system for the accurate anatomical localization of functional activity in the human brain during a neurosurgical procedure. It has been long known that the sensory, motor, and cognitive functions of the brain are organized in anatomically distinct locations. However, with respect to any particular brain function there is considerable variation in anatomical localization between individuals. During a neurosurgical procedure it would be of obvious value to be able to reliably determine whether complete or partial removal of a particular region of the brain would cause a subsequent functional deficit in the patient. For example, before surgical resection, or removal, of a region of abnormal tissue in a patient's temporal lobe causing repeated epileptic seizures, it would be desirable to localize the language region of the particular patient's brain in order not to damage or destroy the subsequent ability of the patient to speak because of inadvertent resection of a functionally active region of tissue in the temporal lobe. Other types of neurosurgical procedures, such as tumor resection, would also benefit from a precise method for functional localization before the neurosurgical procedure is actually performed.

Current methods for localization of brain function may be divided into two general types: invasive and noninvasive. While noninvasive methods of imaging such as positron emission tomography, regional cerebral blood flow, magnetoencephalography, and brain electrical activity mapping have been used for general anatomical localization of brain function, each of these methods has a significant flaw precluding accurate and effective use for localization in the neurosurgical setting. Positron emission tomography, which uses radioactive positron-emitting isotopes such as $^{18}F$-fluorodeoxyglucose to create functional maps of brain metabolism and blood flow, does not possess the spatial resolution necessary for precise neurosurgical localization. Likewise, the measurement of regional cerebral blood flow using $^{133}xenon$ is implemented using large crystal detectors and thus provides very low spatial resolution. The anatomical relationship of non-invasively generated brain electrical and magnetic activity maps to the underlying electrophysiological generators is variable and may be confounded by differences in the spatial orientation of the underlying generators.

There are, however, two invasive methods which are currently used for functional localization in the brain during neurosurgery. These are a) electrocorticographic recording of the electroencephalogram (EEG) and a sensory evoked potentials, and b) electrical stimulation of the brain. During electrocorticography the spontaneous ongoing electrical activity of the brain is monitored using an array of electrodes placed on the surface of the brain and the extremely low-amplitude analog signals, on the order of microvolts, are recorded with galvanometric pens on continuous chart paper. The traces are then analyzed visually and the location of maximum activity or of particular EEG patterns is estimated. Evoked potentials are recorded by monitoring the EEG with an array of electrodes, time-locking digitization of the analog EEG signals to the presentation of a repetitive sensory stimulus, and averaging multiple stimulus trials to reduce background noise. Components of the EEG signal which are temporally synchronized with the stimulus are augmented by the signal averaging process, while components of the EEG which are not temporally synchronized are largely eliminated by the averaging process. Multiple channels of averaged signals are then presented on a video monitor or on chart paper, the traces are analyzed visually, and the location of maximum electrical activity evoked by the sensory stimulus is estimated.

The disadvantage of electrocorticography is that while some spontaneous EEG patterns are well correlated with anatomical landmarks, these patterns may not be present in all patients. Also, for most brain functions of interest no specific EEG pattern has been identified. The disadvantage of recording evoked potentials for neurosurgical localization is that these potentials are mainly useful in defining the somatosensory region, and are of limited use in the localization of other higher brain functions. In addition, both electrocorticography and evoked potential measurements are susceptible to volume conduction effects, in which activity may be recorded at sites relatively distant from the actual electrophysiological generators.

Localization of brain function using electrical stimulation is implemented through the direct application of short current pulses of alternating polarity to different regions of the brain and observing effects of the stimulation on the patient such as muscle twitching during stimulation of the motor region, or obliteration of the ability to speak during stimulation of the language region. Electrical stimulation is useful in the localization of the somatosensory, language, and other regions of higher brain function, but is very time-consuming, and the resolving power of the technique is limited by the size and number of the stimulating electrodes. In addition, the technique of electrical stimulation has been criticized as physiologically artificial, in the sense that being subjected to externally applied electrical current is obviously not a normal physiological condition of the brain. Also, the possibility of current leakage to tissue other than that which is being stimulated cannot be excluded. Finally, the possibility exists that repetitive electrical stimulation of the brain may induce harmful seizures or cause permanent damage to brain tissue.

It is thus obvious that the present state of the neurosurgical art does not offer a dependable, accurate system for localization of brain function which can be used during a neurosurgical procedure. It follows that a system and method for functional localization which combined high spatial resolution, anatomical accuracy, and real time data acquisition and analysis would satisfy an urgent need in current neurosurgical practice. It is the object of the present invention to provide such a system and method.

SUMMARY OF THE INVENTION

The present invention is a system and method for anatomical localization of functional activity in the human brain during neurosurgery. The invention is based on the principle that when a region of the brain is functionally activated by either sensory stimulation of the patient or by the patient's performance of a cognitive task, regional blood flow, regional blood concentration, and regional total hemoglobin concentration all locally increase in the activated area of the brain. (Performance of a cognitive task is possible because neurosurgical patients are often awakened during surgery precisely for the purpose of testing sensory or cognitive responses.) The local increase in blood flow during functional activation is in fact even greater than the increase in other widely used measures of localized brain function such as glucose metabolism, and is thus a highly sensitive indicator of functional activity.

The system and method described here exploits the sensitivity of regional blood flow and blood concentration in brain tissue to functional activation in discrete regions of the brain. The system is comprised of an electronic flash illuminator, optical bandpass filters for sequential illumination of the exposed brain surface with predetermined wavelengths of monochromatic light, a video camera for generating images of the illuminated brain surface, a video processor for conversion of the linear video signal to a log signal directly representing reflectance of the brain surface, an image processor for digitization and analysis of the log-encoded video images and for computation of regional total hemoglobin concentration, a computer and software for control of the entire measurement process, a keyboard and monitor for user interaction with the computer, a high-resolution RGB color video monitor for display of computed functional activity maps, and a stimulus generator for stimulating the patient in order to cause changes in regional total hemoglobin concentration for localizing sensory functional activity of the brain.

The present system and method localizes functional activity by using reflectance spectrophotometry to quantitate regional total hemoglobin (oxyhemoglobin plus deoxyhemoglobin) concentration at a large number of individual points on the surface of the exposed brain during functional activation, and comparing those levels with baseline levels of regional total hemoglobin concentration measured during a preactivation period. A reflectance measurement of regional total hemoglobin concentration is implemented by sequentially illuminating the exposed brain surface with predetermined wavelengths of monochromatic light, acquiring images of the illuminated brain surface at each wavelength with a high-resolution video camera, converting the linear video signal from the camera to a logarithmic signal directly representing reflectance values, digitizing the log-encoded video images and analyzing them using image processing algorithms, and converting the resulting data into maps representing regional total hemoglobin concentration on the brain surface, with each computed map pixel representing a point on a regular grid on the exposed brain surface. By subtracting a map generated during a baseline preactivation period from a map generated during sensory stimulation or cognitive task performance, a third map is generated which represents differences in regional total hemoglobin concentration which have occurred during functional activation. This image is coded, using a standard color- or gray-scale, to represent levels of change in hemoglobin concentration over the exposed brain surface, and is displayed on a high-resolution RGB color video monitor.

The invention thus provides the neurosurgeon with maps of functional activation, in real time, which delineates the regions of the brain which are most active in their response to particular sensory or cognitive stimuli. Regions of the brain which are highly activated manifest large increases in regional blood concentration, while nonactivated regions of the brain show little or no change. The neurosurgeon is thus guided in his decision as to the location and amount of brain tissue he may safely remove.

Advantages of the present invention include higher spatial and temporal resolution than other functional imaging techniques, the ability to analyze the acquired image data and compute maps in real time during the neurosurgical procedure, the elimination of the need for radioactive isotopes or external radiation sources such as x-rays to perform the measurements, the absence of any physical contact between the apparatus and the patient's brain, and a wide range of image resolution and field of view.

DETAILED DESCRIPTION OF THE INVENTION

Figure 1:
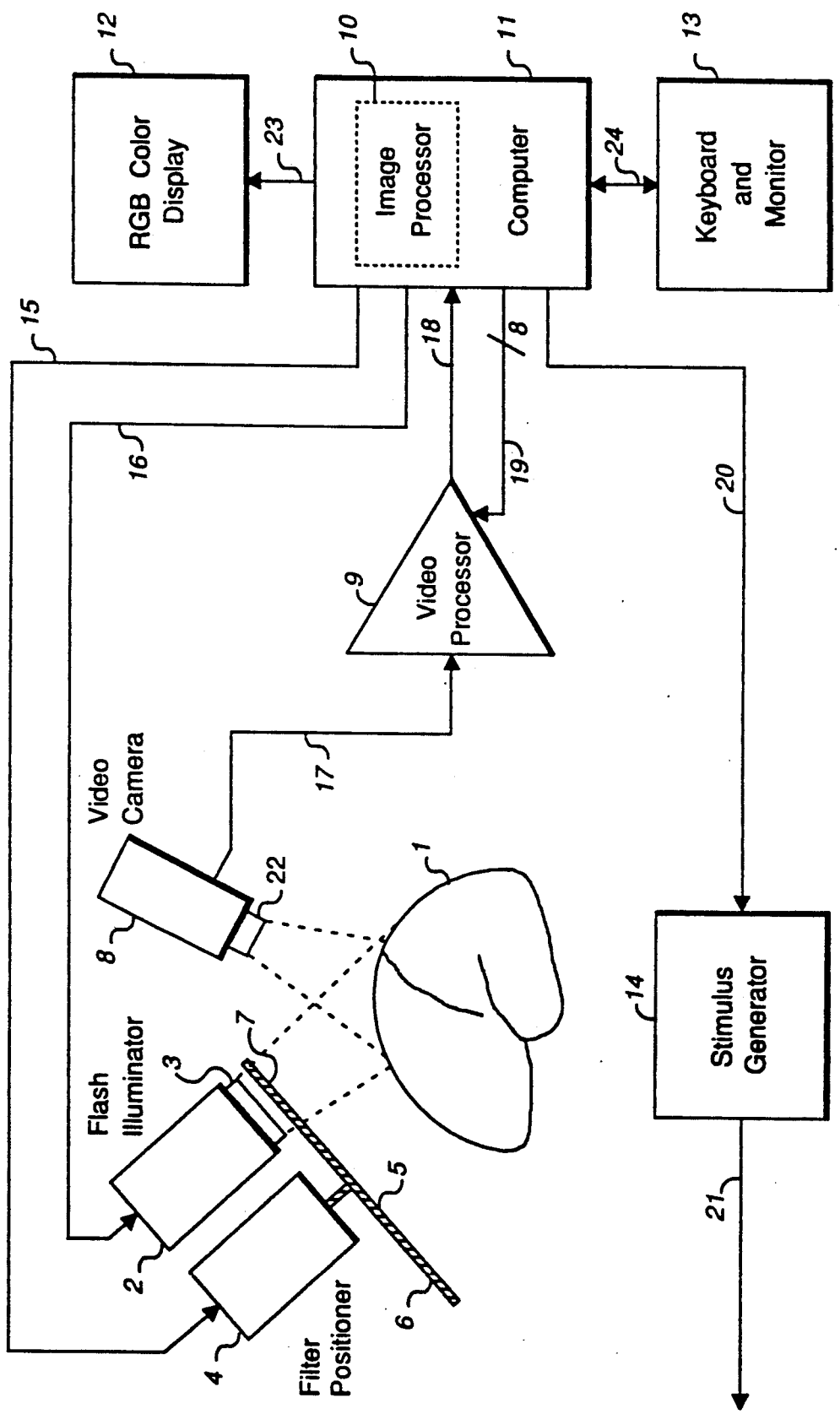
FIG. 1 is a block diagram of the entire system.

FIG. 1 is a block diagram of the present invention. The system comprises an electronic flash illuminator 2 for illuminating the exposed surface of the brain 1, a collimating lens assembly 3 for collimating the light output of the electronic flash, a filter positioner 4 for positioning optical filters in the collimated light beam of the electronic flash illuminator, a filter wheel 5 for holding the optical filters, two optical narrow-bandpass thin-film interference filters 6 and 7, a high-resolution CCD video camera 8 for generating images of the illuminated brain surface, a video processor 9 for conversion of the linear video output signal 17 from the CCD video camera into a logarithmic video signal 18 directly representing units of reflectance, a video frame digitizer, random-access memory, and arithmetic processor 10 for capturing, storing, and performing image processing computations on the logarithmically transformed video signal from the video processor, a computer and software 11 for operation of the image processor and control of image acquisition, analysis, and display, a keyboard and multisync monitor 13 for interaction with the computer, a high-resolution RGB color video monitor 12 for map display, and a multi-mode sensory stimulator 14 for stimulation of the patient.

A detailed description of each section of the system is now presented.

I. Electronic Flash

The electronic flash 2 may be a standard photographic electronic flash unit such as a Vivitar 285HV. Because subsequent filtration of the electronic flash beam by the narrow-bandpass interference filters 6 and 7 significantly attenuates the flash output illumination level, the flash unit must be powerful enough to transmit sufficient light through the filters to allow the use of small lens apertures by the video camera. The use of small lens apertures insures s adequate depth-of-field in the video image of the brain, and the high illumination level minimizes the possibly confounding effect of ambient operating room light on the measurements. A collimator lens assembly 3 is used to collimate the light beam before bandpass filtration, since passage of off-axis light rays through the thin-film interference filters results in a shift of the filter bandpass center frequency. A TTL-level negative-going digital pulse, used to trigger the electronic flash, is provided by an output line 16 from the parallel port of the computer 11. The pulse is applied to the cathode of a photo-silicon controlled rectifier (SCR) opto-isolator, which may be a Harris MCS2400GE, and which electrically isolates the computer circuitry from the high-voltage trigger circuit of the electronic flash. The photo-SCR comprises a light-emitting-diode (LED) and a photosensitive SCR packaged in the same integrated circuit but galvanically isolated from each other. When a digital "0" LOW signal is applied to the cathode of the LED, current flows through the LED, which emits light. The light turns on the optically isolated SCR which in turn triggers the electronic flash. The electronic flash trigger pulse from the computer is synchronized by the system software to coincide with the first line of a new odd field in the video frame. The video camera then outputs a complete video frame (two video fields), which is then processed, digitized and analyzed.

II. Filters and Filter Positioner

Since the method of quantitating hemoglobin in the present invention depends on accurate reflectance measurements at two wavelengths of monochromatic light, two ultra-narrow bandpass filters 6 and 7 are used to filter the electronic flash light illuminating the brain. These filters, produced with thin-film interference technology, may be Ditric custom thin-film interference filters with bandpass center frequencies at 569.0 nm (#ENI 1-0) and 586.0 nm (#ENX 1-0) respectively, with 50% transmission bandwidths of 1.8 nm, and with 10% transmission bandwidths of 2.6 nm. The filters are placed in the illuminating beam of the electronic flash illuminator 2 to produce the monochromatic light needed for accurate spectrophotometric analysis.

The positioner may be a filter wheel 5 with 2 filter apertures. The thin-film interference filters are held in place in the filter wheel apertures by retaining rings which are threaded on their outer circumference and which mate with threads on the inside circumference of the filter wheel apertures. The position of the filter wheel is controlled by a filter positioner 4 which contains a stepping motor driven by a microcontroller board specifically programmed for the task. The stepping motor may be an Airpax L82401 and the microcontroller board may be a Motorola 68HC11 evaluation board. The microcontroller determines the initial position of the filter wheel by monitoring the status of a photosensor which is illuminated by an adjacent light-emitting diode only when a reflective spot on the wheel apparatus is aligned at a unique rotational angle. The computer specifies the position of the filter wheel by writing a digital signal 15 to bit 3 of the parallel port most significant byte, with a "0" selecting the 586 nm filter and a "1" selecting the 569 nm filter. The microcontroller monitors the position bit 15 and positions the filter wheel accordingly.

III. Video Camera

A high-resolution charge-coupled device (CCD) interline-transfer video camera 8, which may be a Sony XC-77, is used to photograph the surface of the brain. The CCD used in this camera is organized as a 768×493 pixel device. The horizontal resolution of the CCD is 380 TV lines, and the overall signal-to-noise ratio of the camera is above 50 dB. Although the CCD used in this camera and in similar industrial grade video cameras are not highly linear in their photometric response, the technique used for image processing in the present system is inherently ratiometric, and photometric nonlinearities in CCD pixel response are thus almost completely removed by the measurement technique.

The camera lens 22, which may be a Nikon 55 mm F/2.8 Micro-Nikkor macro lens, is attached to the video camera with a F-to-C mount adapter. The use of a macro lens originally designed for use with a 35 mm camera insures high resolution, excellent sharpness at both the center and corners of the video frame, and the ability to focus on the brain from short distances for high image magnification when needed, while the telephoto perspective of the lens (when it is used with a video camera) allows routine imaging from a convenient distance in the operating room.

IV. Video Processor

Figure 2:
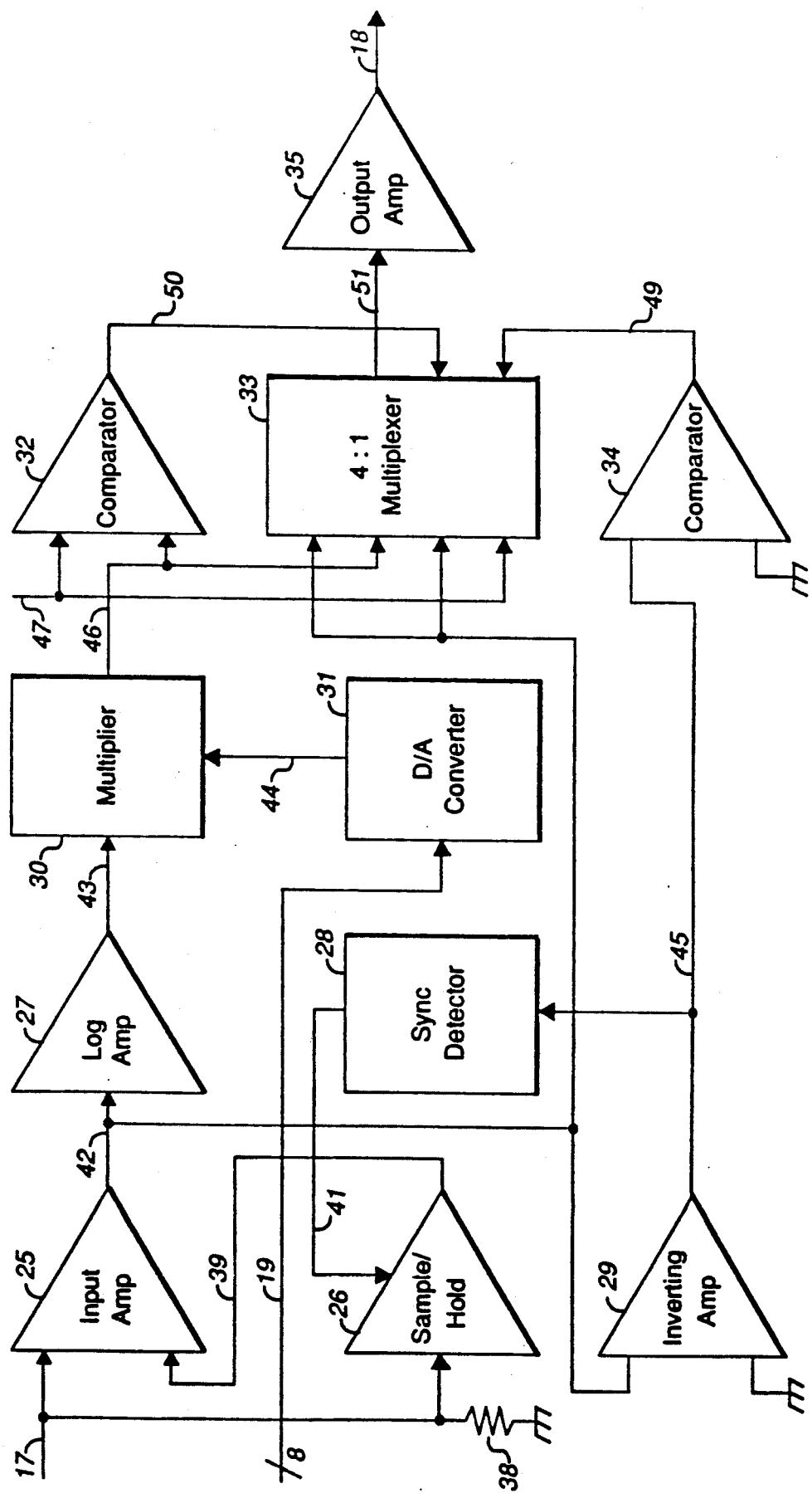
FIG. 2 is a block diagram of the video processor.

FIG. 2 is a block diagram of the video processor 9. The main function of the video processor is to transform the linear output signal 17 from the video camera into a logarithmic signal. There are 3 advantages to the use of logarithmic rather than linear video signals in the present system: 1) Optical absorbance and reflectance are intrinsically ratiometric measurements and are normally expressed as logarithmic units; 2) Log arithmetic replaces multiplication and division operators used in linear frame video arithmetic with addition and subtraction operators respectively, significantly enhancing the speed of video frame arithmetic operations; 3) Using log signals, an equals number of quantization steps (bits) is available at any point on the reflectance vs. voltage scale, while in the digitization of linear reflectance signals most of the quantization steps are clustered at the high end of the scale.

The video processor is comprised of an input video-speed amplifier 25 configured as a differential amplifier and which may be an Analog Devices AD844; a sample-and-hold amplifier 26 which is used as a DC level restoration circuit and which may be a National Semiconductor LF398; a video-speed op amp 29 configured as an inverting amplifier with unity gain and which may be an Analog Devices AD844; a video-speed linear-to-logarithmic amplifier 27 which converts the linear video signal to a logarithmic current output and which may be a Analog Devices AD640; a video-speed op amp 55 (shown in FIG. 3) configured as a current-to-voltage transresistance amplifier and which may be an Analog Devices AD844; a wideband linear multiplier 30 used as a variable-gain amplifier, which is connected to the output of amplifier 55, and which may be an Analog Devices AD539; a video-speed op amp 56 (shown in FIG. 3) configured as a current-to-voltage amplifier which is connected to the output of the wideband multiplier and which may be an Analog Devices AD844; a digital-to-analog-converter 31 whose DC output voltage controls the gain of the variable-gain amplifier and which may be an Analog Devices AD558; an analog multiplexer 33 which both restores horizontal and vertical sync pulses to the log video signal and clamps the log video signal to a preset maximum voltage and which may be an Analog Devices AD9300; a video-speed comparator 32 which sets the clamp voltage for the log video signal and which may be one half of a National Semiconductor LM319; a second video-speed comparator 34 which selects the horizontal and vertical sync pulse inputs to the multiplexer at the appropriate time period in order to restore standard RS-170 sync pulses to the log video waveform and which may be one half of a National Semiconductor LM319; a sync detector 28 which detects vertical and horizontal sync pulses in the linear video signal and which may be a National Semiconductor LM1881; and an output amplifier 35 configured as an inverting amplifier with a gain of −2.00 and an output impedance of 75 ohms and which may be an Analog Devices AD844. The output 18 of the inverting amplifier is connected to the input of the MVP-AT image processor 10 as described below.

A detailed description of the video processor is now presented. The AC-coupled output 17 of the video camera which is in standard RS-170 format is input through a BNC connector and terminated in a 75 ohm resistor 38. The signal is simultaneously input to the inverting input of video-speed amplifier 25 configured in differential amplifier mode with a gain of +1.00 at the noninverting input and −1.00 at the inverting input, and also to the signal input of a sample-and-hold amplifier 26. The sample-and-hold amplifier 26 is switched to SAMPLE mode during the "back porch" period of the video waveform. The output 39 of the sample-and-hold amplifier is connected to the noninverting input of the video-speed amplifier 25, effectively setting the output of the amplifier 25 to a fixed, stable DC voltage level which is independent of the DC component of the input video waveform. A resistor and capacitor (not shown) are configured as a single-pole lowpass filter with a −3 dB point of 235 Hz and connected to the noninverting input of amplifier 25 to smooth switching transients generated by the sample-and-hold amplifier.

Figure 3:
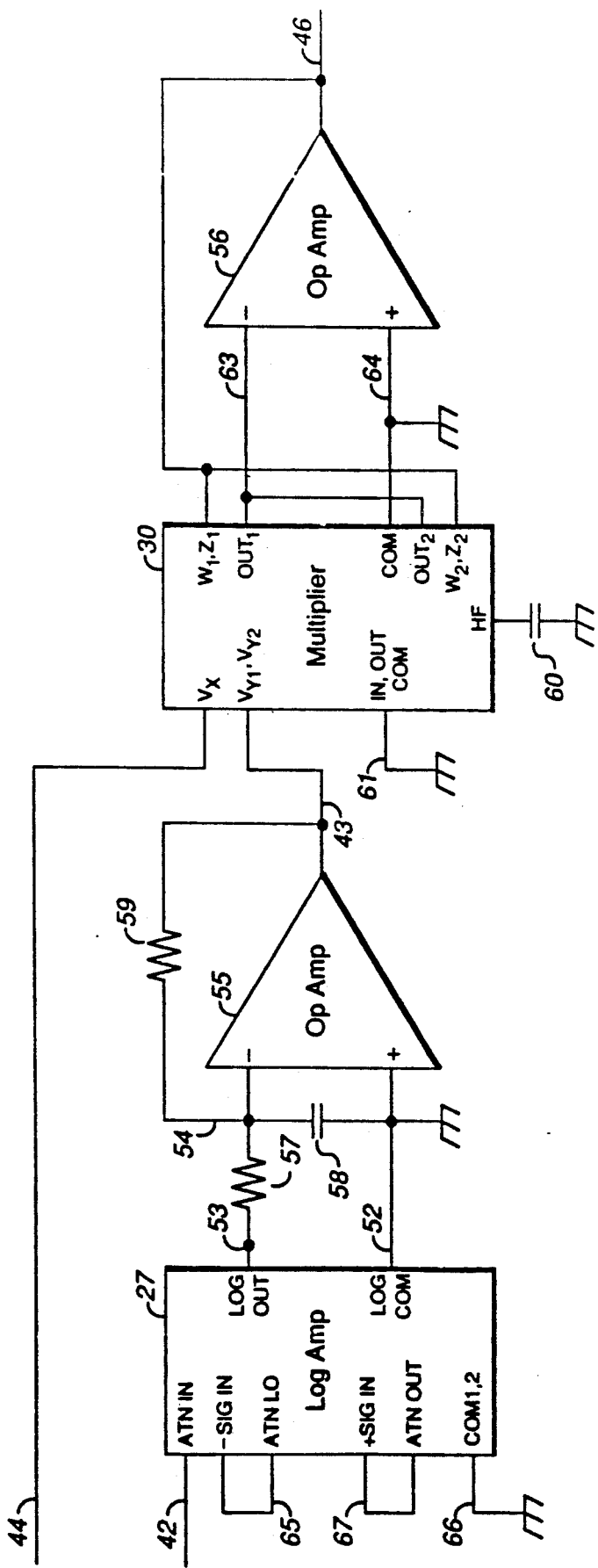
FIG. 3 is a circuit diagram of the variable-slope log amplifier section of the video processor.

FIG. 3 is a circuit diagram of the variable-slope log amplifier section of the video processor. The output of amplifier 25, a signal 42 which is the sum of the inverted input waveform and a fixed DC component, is applied to the attenuator input of the log amplifier 27. The output of the attenuator 67, reduced in amplitude by 20 dB, is applied to the main signal processing section of the log amplifier. Both input common and output common pins 66 of log amplifier 27 are connected to ground. The log common pin 52 is connected to the grounded positive input pin of video-speed amplifier 55. The negative signal input 65 of the log amplifier is connected to the low side of the attenuator differential input. The log amplifier converts the linear signal into a current output 53 proportional to the $\log_{10}$ of the absolute value of the input waveform. The log amplifier current output 53 is filtered by a resistor 57 and capacitor 58 which form a single-pole lowpass filter with a −3 dB point of 15 MHz. The filtered current is applied to the inverting input 54 of video-speed amplifier 55 configured in current-to-voltage transresistance mode, with a precision 1000 ohm resistor 59 setting the voltage gain of the amplifier. Thus, the output of op amp 55 is a voltage proportional to the log of the absolute value of the output signal 42 of amplifier 25. The zero-intercept point of the log response slope is set by a variable resistor (not shown), which adds a fixed DC offset to the output signal of amplifier 25.

The log-transformed video signal is next applied to the variable-gain amplifier section of the circuit. In this circuit application the two channels of the wideband linear multiplier 30 are operated in parallel so that both inputs $V_{Y1}$ and $V_{Y2}$ 43 are connected together and both outputs $OUT_1$ and $OUT_2$ 63 are connected together. The log voltage signal output 43 of op amp 55 is applied to voltage inputs $V_{Y1}$ and $V_{Y2}$ 43 of the multiplier 30. Likewise, both outputs of the multiplier 63 are connected to the inverting input of video-speed op amp 56, which converts the current output of the multiplier to a voltage. The output 46 of op amp 56 is connected to the feedback inputs of the multiplier $W_1$, $W_2$, $Z_1$, and $Z_2$.

The input and output common pins 61 are connected to ground. The base common pin 64 is connected to the grounded positive input of video-speed op amp 56. A 0.1 μF bypass capacitor 60 is used to improve the high-frequency response of the multiplier. The output of this circuit configuration at 46 is $-V_X V_Y/2V$ and is controlled by a positive DC voltage 44 present at the $V_X$ input of the multiplier within the range of 0 to +3.160 VDC. This DC voltage is generated by a digital-to-analog converter 31 whose digital data inputs 19 are connected to outputs D0–D7 of the computer 11 parallel port lower byte. The output 46 of the wideband multiplier is thus the instantaneous product of the log voltage output 43 of log amplifier 27 and the digital value on line 19 present at the inputs to the digital-to-analog converter 31. The multiplier thus directly controls the log response slope of the processing circuit. A high control voltage results in a high-contrast steep log response slope with variations in brain tissue reflectance generating relatively large amplitude differences in the video signal, while a low control voltage results in a low-contrast shallow low response slope, with tissue reflectance variations generating relatively small amplitude differences in the video signal.

It should be noted that at this point in the circuit, the processed signal is inverted with respect to the input signal, and must again be inverted before being connected to the MVP-AT image processor input. In addition, since the output of the processing circuit must conform to RS-170 standards, and since the negative-going sync pulses of the video signal 17 from the camera are highly distorted by the absolute value logarithmic response of the log amplifier 27, sync pulses of correct amplitude and duration must be added to the processed log signal before it is output to the image processor. The addition of sync pulses of correct amplitude and duration to the log-transformed signal is performed by the output multiplexer 33 in conjunction with dual comparators 32 and 34. The output 46 of the multiplier 30 is applied to analog input 2 of multiplexer 33. One of the two multiplexer digital address bits is generated by each of the dual comparators 32 and 34. One comparator 34 generates the lower A0 bit 49 of the multiplexer address input. The negative input of comparator 34 is grounded, and the positive input is connected to the output 45 of video-speed op amp 29 configured as an inverting amplifier with a gain of −1.00. Amplifier 29 reinverts the previously inverted signal output of the input amplifier 25, thus generating a correct-polarity, DC-clamped, linear video signal 45 of the same phase and peak-to-peak amplitude as the input waveform 17. Thus, when the input waveform 45 to the comparator 34 swings below ground during the horizontal and vertical sync pulse periods of the video waveform, the output 49 of the comparator goes low, connecting the output of video amplifier 25, the inverted, DC-restored input waveform 42, to the output 51 of the multiplexer. When the waveform swings above ground, the output of the comparator goes high, connecting the output 46 of the multiplier circuit 30 to the output 51 of the multiplexer. Thus, the output 51 of the multiplexer is the multiplier output combined with composite sync signals of correct amplitude and duration. (However, the polarities of both the signal and sync pulses are inverted). The positive input of the comparator 32 is connected to a voltage divider whose node 47 is held at −1.00 VDC. The output 50 of this comparator controls the high address bit A1 of the multiplexer. Thus, when the multiplier output swings below −1.00 volts, the comparator output goes high, connecting either the composite portion of the input waveform (when A0 is low) or the −1.00 VDC divider voltage (when A0 is high) to the output of the multiplexer. The multiplexer output is thus always clamped to a maximum negative voltage of −1.00 VDC.

The analog output 51 of the multiplexer 33 is applied to the negative input of video-speed op amp 35 configured as an inverting amplifier with a gain of −2.00. Thus, the output 18 of op amp 35 is the log-transformed input video signal 43 multiplied by the slope control voltage 44. The waveform at this point is of proper polarity and has vertical and horizontal sync pulses of s correct amplitude and duration superimposed on it. The signal 18 is connected to the output BNC connector of the video processor through a 75 ohm terminating resistor and a 1000 μF AC-coupling capacitor. The signal is finally connected to analog input channel 0 of the MVP-AT image processor. Since the input resistance of the MVP-AT image processor is 75 ohms, the actual gain of the output amplifier stage is restored to −1.00.

The inverted linear video waveform output of input amp 25 is also applied to an inverting video-speed op amp 29 and the linear reinverted output 45 of amplifier 29 is applied to the input of a video sync detector circuit 28. The sync detector circuit generates separate logic level signals during both composite sync and back porch time periods. The back porch digital signal 41 is applied to the SAMPLE input of sample-and-hold circuit 26, which samples the video waveform during the back porch period and implements DC restoration of the signal at a fixed DC voltage level 39.

V. Image Processor

The analog log-transformed output signal 18 of the video processor 9, in standard RS-170 format, is applied to the video input of the image processor 10, which may be a Matrox MVP-AT with 1 megabyte of memory and which consists of a video-speed analog-to-digital converter, 32 input lookup tables, a random-access memory capable of storing 4 video frames with each video frame consisting of a 512×512×8-bit pixel array, an arithmetic processor capable of performing mathematical operations on a video frame, generally in 1 frame period (30 milliseconds), 32 output lookup tables, 3 digital-to-analog converters at the image processor output 23 which directly drive a high-resolution RGB color video monitor 12, and a high-speed microcomputer embedded in the image processor, which controls imaging functions and processing algorithms. The Matrox MVP-AT frame memory is supplemented by a Ramagette memory board with 4 additional megabytes of random-access memory, allowing the storage of an additional 16 video frames. The image processor and supplementary memory are designed for use on an industry-standard IBM AT (or compatible) computer platform, and in the MS-DOS operating system environment.

Image computation in the image processor is performed using two's complement arithmetic. The input signal from the video processor is therefore converted from the offset binary encoding format of the image processor analog-to-digital converter to two's complement format. This conversion is implemented through a two's complement lookup table stored in one of the input lookup table memories. While the digitized data is initially encoded with 8 bit precision, all subsequent image arithmetic operations are carried out with 16-bit precision in order to allow for two's complement overflow at any step in the computation process. Frame buffers which are normally configured in 8-bit format are therefore reconfigured to 16-bit format during frame arithmetic computations.

The image processor is configured to operate in a conventional manner, the details of which should be readily apparent to persons having ordinary skill in the field of the invention.

VI. Video Data Acquisition and Analysis

The method used for localization of functional brain activity in the present invention is based on the principle that when an area of brain is functionally activated, both regional blood concentration and regional total hemoglobin concentration increase in that area. By creating a baseline map of regional total hemoglobin concentration over the exposed surface of the brain before sensory stimulation of, or cognitive task performance by the patient, and by comparing the baseline map to maps generated at regular intervals during stimulation or task performance, the regions which manifest the greatest change in total hemoglobin concentration can readily be identified.

In the present invention, regional total hemoglobin concentration is quantitated using a spectrophotometric method which is based on the difference in reflectance of brain tissue at two isosbestic wavelengths of hemoglobin. An isosbestic wavelength is one at which the extinction coefficient of two molecules, in this case oxyhemoglobin and deoxyhemoglobin, are identical. Two of the isosbestic wavelengths of hemoglobin are 569 nm and 586 nm. The reflectance of a region of brain tissue illuminated by monochromatic light at a wavelength of 586 nm minus the reflectance of the same region illuminated by monochromatic light at a wavelength of 569 nm is linearly proportional to the total hemoglobin concentration in the region of tissue being measured. This relationship may be expressed as:

$$Hb_n = R586_n - R569_n$$

where Hb is regional total hemoglobin concentration expressed in arbitrary units, n is the elapsed time in seconds from acquisition of the baseline preactivation map, and R is reflectance at the specified isosbestic wavelength of 569 nm or 586 nm. Conversion of arbitrary hemoglobin concentration units to absolute regional concentration is derived by:

$$Hb_n = k \times ((R586_n - R569_n) - b) \mu M/gm$$

where k is a constant calibrated using the individual camera, illuminator, and optical bandpass filters, and b is the baseline value of (R586−R569) determined by measurement of the reflectance of a standard white reference surface which may be Kodak White Reflectance Coating (Catalog 118 1759). The spectrophotometric relationship between total hemoglobin concentration and reflectance is linear over the physiologically useful range of 0.05 μM/gm to 0.40 μM/gm of brain tissue.

As mentioned, the change in total hemoglobin concentration over time is determined by computing successive reflectance maps and subtracting the baseline reflectance map from each of these maps. The result of the subtraction reveals the change in regional total hemoglobin concentration which has occurred during the sensory stimulation or cognitive task performance. Typically, a baseline map $Hb_0$ may be acquired before the start of sensory stimulation and subsequent maps $Hb_{30}$, $Hb_{60}$, $Hb_{90}$ may be computed at regular 30 second intervals. Thus:

$$\Delta Hb_n = Hb_n - Hb_0$$

where $\Delta Hb$ is the change in regional total hemoglobin concentration since the preactivation map was acquired.

Figure 4:
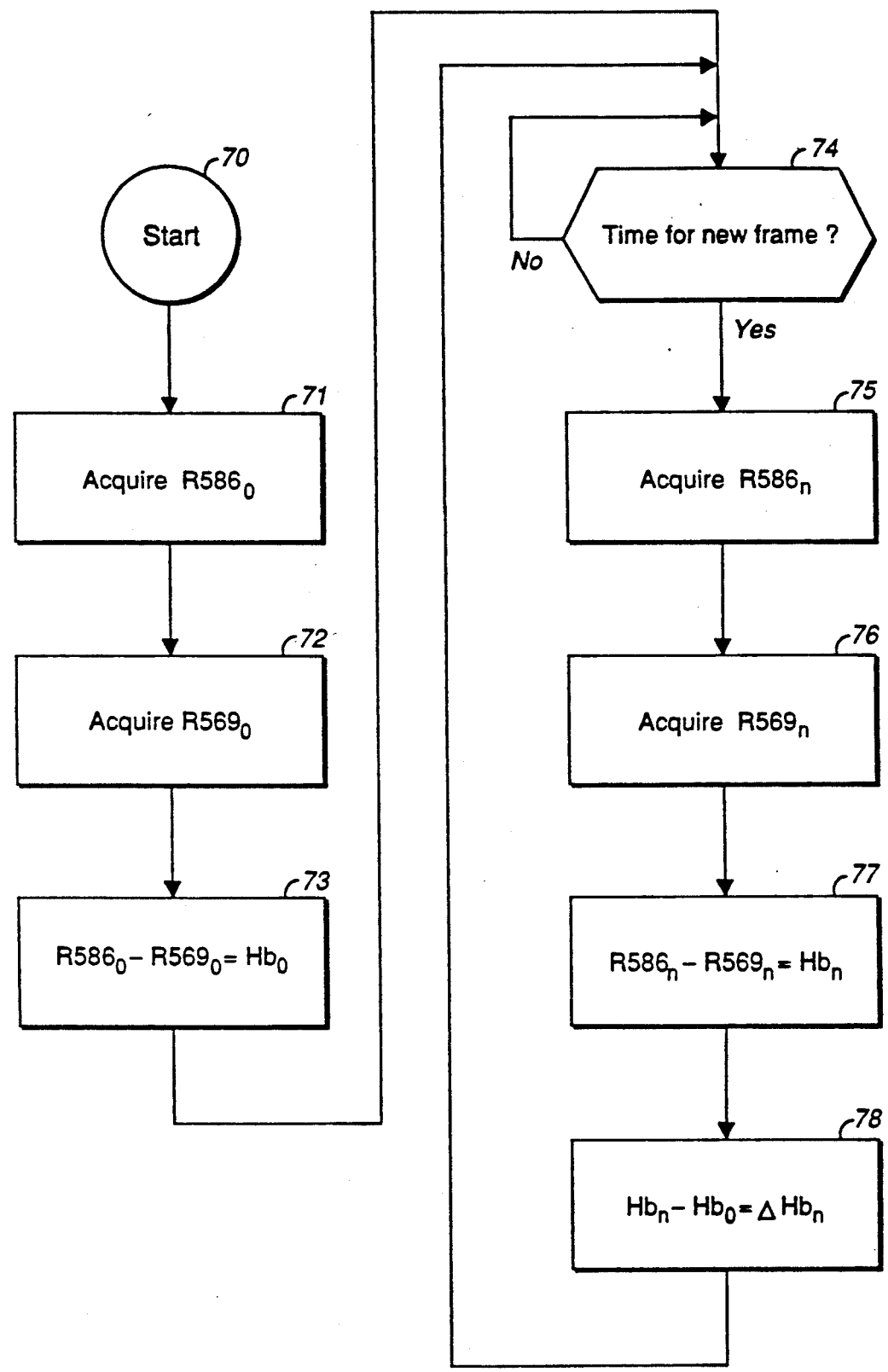
FIG. 4 is a flow chart of the map computation process.

The principle of computing preactivation and postactivation regional total hemoglobin concentration maps is now presented. FIG. 4 depicts a flow chart of map computation. To compute a map, the 586 nm optical bandpass filter is first positioned in the path of the electronic flash illuminator, and the exposed brain surface is illuminated synchronously with the beginning of a new video frame scan. The signal output 17 from the video camera 8 corresponding to the illuminated frame is input to the video processor, which converts the signal from a linear reflectance signal to a log reflectance signal. The log-transformed video signal, whose pixel voltage levels are now each directly proportional to reflectance at the corresponding point on the exposed brain surface, is input to the image processor, which digitizes the complete video frame $R586_0$ 71 and stores it in a section of random-access memory. Next, a command is sent to the filter wheel controller 4 to advance the filter wheel to position the 569 nm optical bandpass filter in the path of illumination. After a suitable delay to allow for filter wheel motion, the exposed brain surface is illuminated synchronously with the beginning of the next complete video frame by the electronic flash illuminator, whose light output is now filtered by 569 nm illumination. This second video frame $R569_0$ is also digitized 72 and stored by the image processor in identical fashion to the first frame. The second video frame is then digitally subtracted, pixel by pixel, from the first video frame using the hardware frame arithmetic capability of the image processor, and the resulting frame $(R586_0 - R569_0 = Hb_0)$ 73, referred to as the baseline regional total hemoglobin map, is stored in image processor random-access memory. The absolute hemoglobin concentration at each map pixel is then easily computed and the map is displayed on the high-resolution RGB color monitor. In addition, since the two frames $R586_n$ and $R569_n$ are illuminated solely at the isosbestic wavelengths of hemoglobin, variations in relative concentrations of oxyhemoglobin and deoxyhemoglobin on the exposed brain surface do not cause errors in the measurement of total light reflectance. It should be noted that among the isosbestic wavelengths of hemoglobin, the choices of 569 nm and 586 nm are particularly useful because other biologically active chromophores, such as those involved in the redox cycle, do not exhibit high absorbance values at these wavelengths, and thus do not appreciably compromise the accuracy of the results.

An example of the method used for map computation during a neurosurgical procedure is now presented. At the start of the neurosurgical procedure the neurosurgeon performs a craniotomy on the patient during which areas of skull and dura covering the region of the brain to be exposed are removed. The operator of the system positions the video camera 8 so that it encompasses the desired field of view and then manually focuses the camera lens 22 while watching the sharpness of the image on the RGB color video monitor 12. During the setup procedure the image processor is operated in continuous acquisition mode, which continuously displays the unprocessed image output of the video camera to allow positioning and focusing the camera. The operator then positions the electronic flash illuminator 2 to evenly illuminate the desired field of view. The electronic flash illuminator may be positioned by either direct measurements relative to the patient's head, or by capturing and displaying illuminated video frames.

Once the video camera and illuminator are positioned satisfactorily, the localization procedure is begun. Before any brain functions are activated using sensory stimulation or cognitive task performance protocols, an initial regional total hemoglobin map $\Delta Hb_0$ representing the preactivation baseline is first acquired 70, 71, 72, 73 using the map acquisition process described above. Based on the brain function to be localized, the neurosurgeon then stimulates the patient appropriately. For example, the sensory motor strip may be activated by tactile stimulation of the patient's hand with a vibrating stimulator which is controlled by the computer. After an appropriate period of activation 74, which will vary for each brain function to be mapped, the procedure described above for acquisition of the baseline map is repeated exactly 75, 76, 77 for acquisition of the postactivation regional total hemoglobin concentration map $Hb_n$ where n is the elapsed postactivation time in seconds. Each successive $Hb_n$ map is stored in frame buffer memory or, for long measurement sequences containing many frames, on a hard disk drive. The baseline map $Hb_0$ is then subtracted from the $Hb_n$ map 78. The resulting map $\Delta Hb_n$ depicts the changes in regional total hemoglobin concentration which have occurred during the sensory stimulation or cognitive task performance periods. Pixel densities on the subtracted image are proportional to changes in reflectance values, and therefore to regional total hemoglobin concentration changes that have occurred during the period of stimulation. In addition, multiple difference images $\Delta Hb_n = Hb_n - Hb_0$ acquired at regular time intervals during the period of stimulation may be calculated and stored to reveal the dynamics of change in regional total hemoglobin concentration over time as stimulation is continued.

VII. Image Processing

In the present system, additional image processing functions are available to supplement the basic functions used for spectrophotometric determination of regional total hemoglobin concentration. As in the case of the basic hemoglobin concentration functions, the additional functions are implemented in hardware by the arithmetic processor board section of the Matrox MVP-AT image processor. The use of hardware for frame computations insures that even those computations which require multiple frame processing steps can be performed in real time, a feature which is required for a system used in the neurosurgical operating room.

A frequently used image processing function available in the present system is an autoscaling function. This function first computes the minimum pixel value present in the current frame buffer map. This minimum value is then subtracted from each pixel in the frame buffer. The maximum pixel value in the frame buffer after subtraction is then found, the fraction of full scale ($2^8 = 256$) it represents is calculated, the inverse of that fraction is determined, and each pixel in the frame buffer is then multiplied by this latter inverse value. The resulting map is scaled to occupy the entire dynamic range of frame buffer pixel values between 0 and 255. The effect is to accentuate small differences in the concentration map which may have been unnoticed in the unscaled map.

Another image processing function is image threshold classification. The threshold function classifies each pixel in the frame buffer into one of two classes: pixels whose values are above a user-specified threshold and pixels whose values are below threshold. If a given pixel value is above threshold, it is displayed in one color, and if the pixel value is below threshold it is displayed in another, preferably contrasting, color. In the present system, pixels whose values are above threshold are displayed in red, while pixels whose values are below threshold are displayed in blue. The visual effect of threshold classification is to produce a high-contrast map clearly delineating regions with hemoglobin concentrations with only slight differences from each other. The resolution of the threshold classification algorithm in the present system is 1 part in 256, or 0.39%. The threshold level is set by the system operator by means of the computer keyboard arrow keys or by directly typing in the numerical value on the keyboard. Threshold classification and display is implemented in the present system by rapidly writing a single red or blue color value into the output lookup tables which are addressed by the pixel values in the frame buffer.

A third image processing function is pixel averaging, which is used to reduce high-frequency noise and enhance the statistical reliability of concentration measurements. In this function, the frame buffer image is convolved with a 3×3 kernel. The convolution is carried out in hardware and lowpass filters the image.

Other image processing algorithms commonly used in the field of the invention, such as edge detection and filtering algorithms, may also be used for enhancement of map images.

VIII. System Software

The control and analysis software for the system is written in the C language, and source code is compiled using the Microsoft C compiler version 6.0. The software performs 4 functions: 1) general control of the system by means of a menu-driven user interface displayed on the multisync monitor 13. FIG. 4 is a flowchart of the menu-driven user interface: 2) configuration and control of image processor operations including configuration of system operating parameters, configuration of input and output lookup tables, initiation and termination of video signal digitization and image acquisition sequences, control of memory storage and retrieval of acquired images, control of sequential image processing operations by the image processor arithmetic hardware, and disk storage of acquired maps together with data headers; 3) computer multisync monitor presentation of operational variables such as stimulus parameters, data file names and presentation of operational variables such as stimulus parameters, data file names and presentation of image histograms computed in real time. The presentation of image histograms allow the system operator to determine whether illumination conditions are adequate for exploitation of the entire dynamic range of the measurement system; 4) control of peripheral system hardware including electronic flash triggering, filter wheel positioning, and log slope setting for the video processor 9.

A complete listing of the system software source code is contained in the Appendix.

IX. Data Display

The video map output of the image processor 10 is displayed in standard analog RGB format, with sync pulses combined with the green video output, on a high-resolution RGB color video monitor 12, which may be a Mitsubishi FA3415ATK. The square 512×512×8-bit pixel image is displayed at a frame rate of 30 per second and a field rate of 60 per second in standard RS-170 interlaced format. The horizontal line rate is 15.75 KHz. The patient name, disk file name of the image, the type of map being displayed, the date, and similar information is retrieved from the disk file data header and displayed at the top of the frame. A color-scale or gray-scale, with 256 separate colors or gray levels, corresponding to the 8-bit deep frame buffer, is usually numerically annotated with hemoglobin concentration values, and is displayed at the bottom of the video frame to allow determination of regional total hemoglobin concentration at any point in the frame. The output lookup tables of the image processor, which are addressed by the frame buffer pixels, are configured so that map pixels with no change or little change from reference values are displayed in gray in the center of the color scale; map pixels with higher regional hemoglobin concentration than those in the reference frame are displayed with increasingly saturated shades of red; and map pixels with lower regional hemoglobin concentration than those in the reference frame are displayed with increasingly saturated shades of blue. This color display scheme results in images in which anatomical landmarks are easily visible while regional total hemoglobin concentration values appear to be overlaid on the brain map.

Aside from the difference maps, the operator may choose to view the baseline prestimulation maps, any map acquired during the stimulation or cognitive task performance interval, or a simple video image of the brain.

In addition, since the random-access memory of the image processor permits storage of 20 total frames of data, a continuous loop of sequentially acquired frames may be displayed at the user's option, resulting in a dynamic view of change in regional total hemoglobin concentration after the start of stimulation or cognitive task performance.

X. Stimulus Generator

A stimulus generator 14 contains circuitry for stimulation of the various sensory pathways. These include trigger outputs for tactile stimulators, for LED spectacles, and for earphones. Stimulus modality and parameters are controlled by the computer 11. For example, tactile stimulation may be produced by a vibration device taped to the patient's hand and vibrating against the patient's skin. Auditory stimulation is generated by a click or tone audio output of the stimulator with programmable frequency, amplitude, and duration. Delivery of the stimulus and the temporal relationship between stimulus delivery and map acquisition is controlled by the computer. A typical protocol might consist of acquisition of a baseline map followed by continuous tactile stimulation using a vibration device taped to the patient's arm with acquisition of a new regional total hemoglobin concentration map every 30 seconds.

Alternatively, cognitive tasks similar to those utilized in position emission tomographic studies of cognition may be performed by the patient in neuropsychological paradigms appropriately modified for the neurosurgical setting. Acquisition of successive maps at 30 second intervals, similar to the protocol used for sensory stimulation and mapping, may be used for cognitive task performance and mapping.

APPENDIX: SYSTEM SOURCE CODE

```c
/******************************************************************
 *                                                                *
 *          REGIONAL TOTAL HEMOGLOBIN CONCENTRATION               *
 *                                                                *
 *          MAPPING SYSTEM:   VERSION 1.0                         *
 *                                                                *
 ******************************************************************/

/*      Include Header Files    */ include <stdmvp.h>
include <im2to3.h>
#include <debugat.h>
#include <stdlib.h>
#include <stdio.h>
#include <conio.h>
#include <inkey.h>
#include <string.h>
#include <graph.h>
#include <pgchart.h>
#include <bios.h>
#include <math.h>
#include <time.h>

/*      Variable Initialization    */ int sourcebuffer  =   0;
int overlaybuffer =   0;
int rambuffer     =   0;
int deltapointer  =   0;
int direction     =   0;
int flashnumber   =   0;
int filternumber  =   0;
int autoflag      =   0;
int slopenumber   =   0;
int keynumber     =   0;

int offsetvalue   =   0;
int gainvalue     =   0;

long delayvalue   =   0;
long blanktimer   =   0;

int frametype     =   0;
int ilutype       =   0;
int oluttype      =   0;
int histindex     =   0;
int screenstatus  =   0;
int timeout       =   0;
int lastscreen    =   0;
int scaleflag     =   0;
int autoscaleflag =   0;
int averageflag   =   0;
int frametitleflag = 0;
int histflag      =   0;
int oldcolor      =   0;
int nybble        =   0;
int lutsource     =   0;
int lutnum        =   0;
int selectflag    =   0;
int palettenumber =   0;
int threshvalue   = 128;
```

```c
int timeflag =         0;
time_t start =         0;
time_t current_time =  0;
time_t frame_time =    0;
time_t last_time =     0;
double elapsed_time =  0;

int data_valid[ FRAMETYPES ];
unsigned long histbuf[ HISTSIZE_8 + 2 ];
float histvalue [ FRAMETYPES ] [ HISTSIZE_8 ];
float intenvalue[ HISTSIZE_8 ];
float ymaxvalue[ FRAMETYPES ];
float yminvalue[ FRAMETYPES ];

char filename[ _MAX_FNAME ];
char pathname[ _MAX_PATH ];

char headerbuffer[ NUMXPIXELS ];
char *headerpointer;

char textbuffer[ LASTCOL ];
char gtextbuffer[ LASTCOL ];
char commandstring[ 10 ];

unsigned char outputregl = 0x00;
unsigned char outputregh = 0x00;

union k
  {
    char ch[ 2 ];
    unsigned i;
  } inputkey;

typedef enum { FALSE, TRUE } boolean;
palettetype pal;
chartenv env;

/***************************
*                          *
*    Main Program Loop     *
*                          *
***************************/ main(argc, argv )
  int argc;
  char *argv[];
    {
      char ch;
      int endflag = 0;

init( MEM_SEG, IO_BASE );
      init_ram();
      init_video();
      init_gamma();
      init_frame_buffers();
      init_palettes();
      init_data_valid_flags();
      init_outport();
      init_vga_screen();

while( ! endflag )
        {
          if( _bios_keybrd( _KEYBRD_READY ) )
            {
              inputkey.i = _bios_keybrd( _KEYBRD_READ );

blanktimer = 0;
```

```
            case F3:
              store_data_file();
              break;

case F4:
              retrieve_data_file();
              break;

case F5:
              set_image_threshold();
              break;

case F6:
              toggle_autoscale();
              break;

case F7:
              toggle_average();
              break;

case F8:
              get_continuous_frames( FB0 );
              break;

case F9:
              toggle_screen();
              break;

case F10:
              _clearscreen( _GWINDOW );
              _setvideomode(_DEFAULTMODE);
              _settextcolor( oldcolor );
              printf( "\033[33m" );

opmode( PROCESS, sourcebuffer );
              video_off();

endflag = 1;
              break;

case F11:
               toggle_log_slope();
               break;
          }
      }
   else
      {
        blanktimer = blanktimer + 1;

if( blanktimer == BLANKTIME )
           {
             timeout = 1;
             lastscreen = screenstatus;
             screenstatus = BLANKED - 1;
             toggle_screen();
           } if( blanktimer > BLANKTIME )
           blanktimer = BLANKTIME + 1;

if( timeflag )
           {
             time( &current_time );

if( difftime( last_time, current_time) )
                {
                  write_current_time();
```

```
                last_time = current_time;
            }
        }
    }
    exit( 0 );
}

/**********************************************
*                                             *
*      Blood Flow Measurement Functions       *
*                                             *
**********************************************/ compute_reference_frame()
    {
        write_command( "REFERENCE" );

init_data_valid_flags();
        deltapointer = R_DELTA - 2;

get_filtered_frames( MANUAL );
        get_reference_time();
        confirm_acquisition();

sign_extend( FB0 );
        sign_extend( FB2 );

compute_background_frame();
        interimage( FB4, FB5, FB4, SUB );

transfer_frame( R_WRITE, FB1, R_REFERENCE );
        transfer_frame( R_WRITE, FB0, R_REFERENCE - 1 );

image( FB4, FB4, ADD, 256, PRECISION_12 );
        image( FB4, FB4, DIV, 2, PRECISION_12 );
        clear( FB3, BLACK );
        interimage( FB0, FB3, FB3, ADD );

compute_histogram( REFERENCE );
        data_valid[ REFERENCE ] = 1;
        confirm_computation();
        write_current_time();
        write_blank_frame_time();

display_frame( FB3, MINUSVALUE, REFERENCE, SCALEOFF );
    } retrieve_reference_frame()
    {
        transfer_frame( R_READ, FB1, R_REFERENCE );
        transfer_frame( R_READ, FB0, R_REFERENCE - 1 );

image( FB4, FB4, ADD, 256, PRECISION_12 );
        image( FB4, FB4, DIV, 2, PRECISION_12 );
        clear( FB3, BLACK );
        interimage( FB0, FB3, FB3, ADD );
    }
compute_delta_frame( autoflag )
   int autoflag;
    {
        get_filtered_frames( MANUAL );
        sign_extend( FB0 );
        sign_extend( FB2 );
        interimage( FB4, FB5, FB4, SUB );

deltapointer = deltapointer + 2;
```

```
        if( deltapointer >= ( R_DELTA + ( R_DELTA_COUNT * 2 ) ) )
          deltapointer = R_DELTA;

transfer_frame( R_WRITE, FB1, deltapointer );
        transfer_frame( R_WRITE, FB0, deltapointer - 1 );

clear( FB5, BLACK );
        interimage( FB4, FB5, FB5, ADD );
        image( FB5, FB5, ADD, 256, PRECISION_12 );
        image( FB5, FB5, DIV, 2, PRECISION_12 );

compute_histogram( DELTA );
        data_valid[ DELTA ] = 1;
        confirm_acquisition();
        write_current_time();
        write_frame_time();

clear( FB5, BLACK );
        interimage( FB4, FB5, FB5, ADD );
    } retrieve_delta_frame()
    {
        transfer_frame( R_READ, FB3, deltapointer );
        transfer_frame( R_READ, FB2, deltapointer - 1 );

image( FB5, FB5, ADD, 256, PRECISION_12 );
        image( FB5, FB5, DIV, 2, PRECISION_12 );
    } compute_map_frame()
    {
        if( ! data_valid[ REFERENCE ] )
          return( 0 );

write_command( "MAP" );

compute_delta_frame();

transfer_frame( R_READ, FB1, R_REFERENCE );
        transfer_frame( R_READ, FB0, R_REFERENCE - 1 );

interimage( FB4, FB5, FB4, SUB );
        image( FB4, FB4, ADD, 512, PRECISION_12 );
        image( FB4, FB4, DIV, 4, PRECISION_12 );
        compute_histogram( MAP );
        data_valid[ MAP ] = 1;
        confirm_computation();

display_frame( FB0, MINUSVALUE, MAP, SCALEON );
    } retrieve_map_frame()
    {
        transfer_frame( R_READ, FB1, R_REFERENCE );
        transfer_frame( R_READ, FB0, R_REFERENCE - 1 );

transfer_frame( R_READ, FB3, deltapointer );
        transfer_frame( R_READ, FB2, deltapointer - 1 );

interimage( FB4, FB5, FB4, SUB );
        image( FB4, FB4, ADD, 512, PRECISION_12 );
        image( FB4, FB4, DIV, 4, PRECISION_12 );
    }
```

```
compute_background_frame()
    {
        transfer_frame( R_WRITE, FB1, R_BACKGROUND );
        transfer_frame( R_WRITE, FB0, R_BACKGROUND - 1 );
        image( FB0, FB1, ADD, 128, PRECISION_12 compute_histogram( BACKGROUND );
        data_valid[ BACKGROUND ] = 1;

transfer_frame( R_READ, FB1, R_BACKGROUND );
        transfer_frame( R_READ, FB0, R_BACKGROUND - 1 );
    } retrieve_background_frame()
    {
        transfer_frame( R_READ, FB1, R_BACKGROUND - 1 );
        image( FB1, FB1, ADD, 128, PRECISION_12 );
    } sign_extend( sourcebuffer )
  int sourcebuffer;
    {
        slut( INPUT, LUT2 );
        clear( sourcebuffer + 1, BLACK );
        interimage( sourcebuffer, sourcebuffer + 1,
          sourcebuffer + 1, ADD );
        inmap( sourcebuffer + 1, sourcebuffer + 1, 0 );
        slut( INPUT, LUT1 );
    }
/****************************************************
*                                                    *
*    Video Acquisition and Display Functions         *
*                                                    *
****************************************************/ get_filtered_frames( autoflag )
  int autoflag;
    {
        if( autoflag )
          {
            select_filter( NM_586 );
            get_frame( FB0 );

select_filter( NM_569 );
            get_frame( FB2 );
          }
        else
          {
            wait_for_start_key( 0 );
            get_frame( FB0 );

wait_for_start_key( 1 );
            get_frame( FB2 );
          }
    } get_frame( sourcebuffer )
  int sourcebuffer;
    {
        opmode( PROCESS, sourcebuffer);
        video_off();

wait_for_frame_start();
        trigger_flash( 0 );
        snapshot( sourcebuffer );
```

```
      clear_last_row( sourcebuffer );
   } get_continuous_frames( sourcebuffer )
   int sourcebuffer;
      {
         screenstatus = REFERENCE;
         toggle_screen();
         write_command( "FOCUS" );
         set_menu_window();
         clear_message();
         _settextcolor( BRIGHTWHITE );
         _outtext( "Please wait... " );

opmode( PROCESS, sourcebuffer );
         video_off();
         init_linear_grayscale_lut( INPUT, LUT0, SELECT );
         outpath( sourcebuffer, MINUSVALUE, FB2, MSB );
         outpath( sourcebuffer, MINUSVALUE, FB2, MSB );
         init_linear_overlut( OUTPUT, 16, DESELECT );
         draw_grid( FB2 );
         video_on();

opmode( CGRAB, sourcebuffer );
         cgrab( MINUSVALUE );
         wait_for_end_key();
         cgrab( DISABLE );
         clear_last_row( sourcebuffer );
         opmode( PROCESS, sourcebuffer );

init_twoscomp_grayscale_lut( INPUT, LUT1, SELECT );
      } transfer_frame( direction, sourcebuffer, rambuffer )
   int direction, sourcebuffer, rambuffer;
      {
         video_off();
         opmode( PROCESS, FB0 );
         disformat( RECTANGLE, INTERLACED, AMERICAN );

opmode( CGRAB, FB0 );
         ram_switch( R_ON );
         cgrab( DISABLE );

if( ! direction )
            ram_fromframe( sourcebuffer, rambuffer );
         else
            ram_toframe( rambuffer, sourcebuffer );

opmode( CGRAB, FB0 );
         ram_switch( R_OFF );
         cgrab( DISABLE );

opmode( PROCESS, FB0 );
         disformat( SQUARE, INTERLACED, AMERICAN );
      } display_frame( sourcebuffer, overlaybuffer, frametype, scaleflag )
   int sourcebuffer, overlaybuffer, frametype, scaleflag;
      {
         if( overlaybuffer == MINUSVALUE )
            {
               slut( OUTPUT, LUT0 );
               outpath( sourcebuffer, MINUSVALUE, NONE, NONE );
            }
```

```
    else
      {
        slut( OUTPUT, LUT16 );
        outpath( sourcebuffer, MINUSVALUE, overlaybuffer, MSB );
        outpath( sourcebuffer, MINUSVALUE, overlaybuffer, MSB );
      }
    write_frametitle( sourcebuffer, frametype, FRAMETITLEON );

if( scaleflag )
      write_intensity_scale( sourcebuffer );

screenstatus = frametype;
    video_on();

display_histogram( HISTON, frametype );
    write_data_values( frametype );
  } toggle_screen()
    {
      screenstatus = screenstatus + 1;

if( screenstatus == FRAMETYPES )
        screenstatus = MAP;

if( data_valid[ screenstatus ] )
        {
          video_off();
          switch( screenstatus )
            {
              case MAP:
                retrieve_map_frame();
                display_frame( FB0, MINUSVALUE, MAP, SCALEON );
                break;

case BACKGROUND:
                retrieve_background_frame();
                display_frame( FB1, MINUSVALUE, BACKGROUND, SCALEOFF );
                break;

case DELTA:
                retrieve_delta_frame();
                display_frame( FB2, MINUSVALUE, DELTA, SCALEOFF );
                break;

case REFERENCE:
                retrieve_reference_frame();
                display_frame( FB3, MINUSVALUE, REFERENCE, SCALEOFF );
                break;

case BLANKED:
                display_histogram( HISTOFF, 0 );
                break;
            }
        }
    }
init_frame_buffers()
    {
      clear( FB4, BLACK );
      clear( FB5, BLACK );
    } video_on()
    {
      video( ENABLE, FRAMEBUFFER );
    }
```

```
video_off()
    {
      video( DISABLE, FRAMEBUFFER );
    } clear_last_row( sourcebuffer )
  int sourcebuffer;
    {
      unsigned int buf[ NUMXPIXELS ];
      unsigned char lbbuf[ NUMXPIXELS ];

scaling( 0, 0, ( NUMXPIXELS - 1 ), 0, buf );
      cwb( buf, lbbuf, NULL, NUMXPIXELS );
      opmode( IO, sourcebuffer );
      roww( 0, ( NUMYPIXELS -1 ), NUMXPIXELS, lbbuf );
      opmode( PROCESS, sourcebuffer );
    } init_gamma()
    {
      offset( MVPOFFSET );
      offsetvalue = MVPOFFSET;
      gain( MVPGAIN );
      gainvalue = MVPGAIN;
    } set_brightness()
    {
      int oldval, temp;

write_command( "BRIGHT");

do
        {
          clear_message();
          sprintf( textbuffer, "Enter brightness value ( %d ): ",
                               offsetvalue );
          _outtext( textbuffer );
          scanf( "%d", &temp);
          fflush( stdin );
        }
      while( temp < 0 || temp > FULLSCALE );
      offsetvalue = temp;
      clear_message();
      sprintf( textbuffer, "New brightness value is %d.", offsetvalue );
      _outtext( textbuffer );

offset( offsetvalue );
    } set_contrast()
    {
      int oldval, temp;

write_command( "CONTRAST" );
      do
        {
          clear_message();
          sprintf( textbuffer, "Enter contrast value ( %d ): ", gainvalue );
          _outtext( textbuffer );
          scanf( "%d", &temp);
          fflush( stdin );
        }
      while( temp < 0 || temp > FULLSCALE );
      gainvalue = temp;
      clear_message();
```

```c
        sprintf( textbuffer, "New contrast value is %d.", gainvalue );
        _outtext( textbuffer );

gain( gainvalue );
    } toggle_log_slope()
    {
        unsigned char slopevalue = 0;

slopenumber = slopenumber + 1;

if( slopenumber == 4 )
           slopenumber = 0;

switch( slopenumber )
           {
              case 0:
                 slopevalue = 0x3F;
                 break;

case 1:
                 slopevalue = 0x7F;
                 break;

case 2:
                 slopevalue = 0xBF;
                 break;
              case 3:
                 slopevalue = 0xFF;
                 break;
           }
        outp( OUTPORT_L, slopevalue );
    } wait_for_frame_start()
    {
        char status_val;

do
           {
              status_val = ll_status() & 0x06;
           }
        while( status_val != 2 );

do
           {
              status_val = ll_status() & 0x06;
           }
        while( status_val != 6 );
    } trigger_flash( flashnumber )
    int flashnumber;
    {
        unsigned char byte_value;

outputregh = 0xFF;
        byte_value = outputregh & 0x00;
        outp( OUTPORT_H, byte_value );
        delay( 333L );
        byte_value = outputregh | 0xFF;
        outp( OUTPORT_H, byte_value );
    } select_filter( filternumber )
```

```
int filternumber;
  {
    unsigned char filtervalue;

switch ( filternumber )
      {
        case NM_586:
        filtervalue = 0x00;
        break;

case NM_569:
        filtervalue = 0x04;
        break;
      }
    outp( OUTPORT_H, filtervalue );
  }
init_video()
    {
      opmode( PROCESS, FB0 );
      disformat( SQUARE, INTERLACED, AMERICAN );
      sync( EXTERNAL, COMPOSITE );
      outmode( CLEAN );
      outpath( FB0, MINUSVALUE, NONE, NONE );
      inmode( BW );
      chan( CH0 );
    } init_ram()
    {
      opmode( CGRAB, FB0 );
      cgrab( MINUSVALUE );
      ram_init( IMAGES_16, R_OFF, AMERICAN );
      ram_mode( R_OFF, R_STILL, R_STARTSTOP, R_INTERLACED, R_EVEN );
      cgrab( DISABLE );
      opmode( PROCESS, FB0 );
    } init_outport()
    {
      outputregh = 0xFF;
      outp( OUTPORT_H, 0xFF );
      outputregl = 0xFF;
      outp( OUTPORT_L, 0xFF );
    } init_data_valid_flags()
    {
      data_valid[ MAP ] = 0;
      data_valid[ BACKGROUND ] = 0;
      data_valid[ DELTA ] = 0;
      data_valid[ REFERENCE ] = 0;
      data_valid[ BLANKED ] = 1;
    } delay( delayvalue )
  long delayvalue;
    {
      int x;
      long delaytimer;

for( delaytimer = 0; delaytimer < delayvalue; delaytimer++ )
        x = delaytimer / 2 ;
    }
```

```
/****************************************
 *                                      *
 *     Video Processing Functions       *
 *                                      *
 ****************************************/ autoscale_frame( sourcebuffer )
  int sourcebuffer;
     {
        int minvalue, maxvalue, scalefactor;

minvalue = find_minimum( sourcebuffer );
        image( sourcebuffer, sourcebuffer, SUB, minvalue, PRECISION_12 );
        maxvalue = find_maximum( sourcebuffer );

if( maxvalue )
           {
              clear( FB1, BLACK );
              image( sourcebuffer, FB0, ADD, 0, PRECISION_12 );
              image( FB4, FB4, MUL, ( FULLSCALE - 1 ), PRECISION_12 );
              image( FB4, FB4, DIV, maxvalue, PRECISION_12 );
              image( FB0, sourcebuffer, ADD, 1, PRECISION_12 );
           }
     } find_minimum( sourcebuffer )
     {
        int minvalue;

minvalue = minimum( sourcebuffer );
        disformat( SQUARE, INTERLACED, AMERICAN );
        return( minvalue );
     } find_maximum( sourcebuffer )
     {
        int maxvalue;

maxvalue = maximum( sourcebuffer );
        disformat( SQUARE, INTERLACED, AMERICAN );
        return( maxvalue );
     } average_frame( sourcebuffer )
     {
        average( sourcebuffer, FB4 );
     } set_image_threshold()
     {
        unsigned char redbuf[ LUTSIZE ], greenbuf[ LUTSIZE ],
          bluebuf[ LUTSIZE ];
        int ch = 0;
        float temp;

_settextcolor( BRIGHTWHITE );
        write_command( "THRESHOLD" );

temp = ( threshvalue / 255.0 ) * 100;
        set_data_window();
        clear_data( 16 );
        _settextposition( 16, 1 );
        sprintf( textbuffer, "Threshold:      [%3d]  %6.2f %% ",
                 threshvalue, temp );
```

```
   _outtext( textbuffer );

slut( OUTPUT, LUT2 );

redbuf[ ZERO ] = ZERO;
   greenbuf[ ZERO ] = ZERO;
   bluebuf[ ZERO ] = ZERO;

redbuf[ FULLSCALE ] = FULLSCALE;
   greenbuf[ FULLSCALE ] = FULLSCALE;
   bluebuf[ FULLSCALE ] = FULLSCALE;

wlut( OUTPUT, LUT2, 0, LUTSIZE, redbuf, greenbuf, bluebuf );

set_threshold_lut( threshvalue );

while ( ch != K_CR && ch != 3 )
      {
        while ( ( ch = mv_inkey() ) == 0 );
          switch( ch )
            {
              case K_UP:
                ++threshvalue;
                break;
              case K_DOWN:
                --threshvalue;
                break;
              case K_PGUP:
                threshvalue += 16;
                break;
              case K_PGDN:
                threshvalue -= 16;
                break;
            } if ( threshvalue > ( FULLSCALE - 1) )
          threshvalue = ( FULLSCALE - 1 );

if ( threshvalue < 1 )
          threshvalue = 1;

temp = ( threshvalue / 255.0 ) * 100;

set_data_window();
        _settextposition( 16, 17 );
        sprintf( textbuffer, "[%3d]  %6.2f %% ", threshvalue, temp );
        _outtext( textbuffer );

set_threshold_lut( threshvalue );
      } set_data_window();
   _settextposition( 16, 1 );
   sprintf( textbuffer, "                                      " );
   _outtext( textbuffer );
   slut( OUTPUT, LUT0 );
  } set_threshold_lut( threshvalue )
  int threshvalue;
    {
      int i;
      unsigned char redbuf[ LUTSIZE ], greenbuf[ LUTSIZE ],
        bluebuf[ LUTSIZE ];
```

```
   for ( i = threshvalue; i < ( FULLSCALE - 1 ); i++ )
     {
       redbuf[ i ] = 0xFF;
       greenbuf[ i ] = 0x00;
       bluebuf[ i ] = 0x00;
     } for ( i = 1; i < threshvalue; i++ )
     {
       redbuf[ i ] = 0x00;
       greenbuf[ i ] =0x00;
       bluebuf[ i ] = 0xFF;
     } wblank();
   wlut( OUTPUT, LUT2, 1, ( LUTSIZE - 2 ), redbuf, greenbuf, bluebuf );
  } toggle_autoscale()
   {
     retrieve_map_frame();

if( autoscaleflag )
        autoscaleflag = 0;
     else
       {
         autoscaleflag = 1;
         autoscale_frame( FB0 );
       } screenstatus = BLANKED;
     toggle_screen();
   } toggle_average()
   {
     retrieve_map_frame();

if( averageflag )
       {
         averageflag = 0;
       }
     else
       {
         averageflag = 1;
         average_frame();
       } screenstatus = BLANKED;
     toggle_screen();
   } multiply_buffer()
    {
      short int rownum, colnum;
      unsigned char rowbuf[ NUMXPIXELS ];
      unsigned int workbuf[ NUMXPIXELS ];

opmode( IO, sourcebuffer );
      for( rownum = 0; rownum < NUMXPIXELS; rownum++ )
```

```
        {
            rowr( 0, rownum, NUMXPIXELS, rowbuf );

for( colnum = 0; colnum < NUMXPIXELS; colnum++ )
                rowbuf[ colnum ] = 0.5 * rowbuf[ colnum ] ;

roww( 0, rownum, NUMXPIXELS, rowbuf );
        }
        opmode( PROCESS, sourcebuffer );
    }

/***************************
 *                         *
 *    Palette Functions    *
 *                         *
 ***************************/ init_palettes()
    {
        init_linear_grayscale_lut( INPUT, LUT0, DESELECT );
        init_twoscomp_grayscale_lut( INPUT, LUT1, SELECT );
        init_sign_extension_lut( INPUT, LUT2, DESELECT );
        init_linear_grayscale_lut( OUTPUT, LUT0, SELECT );
        init_linear_colorscale_lut( OUTPUT, LUT1, DESELECT );
        palettenumber = 0;
        toggle_output_palette();
    } toggle_output_palette()
    {
        palettenumber = palettenumber + 1;

if( palettenumber == PALETTETYPES )
            palettenumber = LINGRAY;

switch( palettenumber )
          {
            case LINGRAY:
                init_linear_grayscale_lut( OUTPUT, LUT0, SELECT );
                break;

case LINCOLOR:
                init_linear_colorscale_lut( OUTPUT, LUT0, SELECT );
                break;

case LOGGRAY:
                init_log_grayscale_lut( OUTPUT, LUT0, SELECT );
                break;
          }
    } init_linear_grayscale_lut( lutsource, lutnum, selectflag )
  int lutsource, lutnum, selectflag;
    {
        unsigned int buf[ LUTSIZE ];
        unsigned char lbbuf[ LUTSIZE ], hbbuf[ LUTSIZE ];

scaling( 0, 0, FULLSCALE, FULLSCALE, buf );
        cwb( buf, lbbuf, NULL, LUTSIZE );
```

```
      if( ! lutsource )
         invert( LUTSIZE, lbbuf );

wlut( lutsource, lutnum, 0, LUTSIZE, lbbuf, lbbuf, lbbuf );
      if( selectflag )
         slut( lutsource, lutnum );
   } init_twoscomp_grayscale_lut( lutsource, lutnum, selectflag )
   int lutsource, lutnum, selectflag;
   {
      unsigned int buf[ LUTSIZE ];
      unsigned char lbbuf[ LUTSIZE ];

scaling( 0, 128, 127, 255, buf );
      scaling( 128, 0, 255, 127, buf );
      cwb( buf, lbbuf, NULL, LUTSIZE );

lbbuf[ 0 ] = 129;

if( ! lutsource )
         invert( LUTSIZE, lbbuf );

wlut( lutsource, lutnum, 0, LUTSIZE, lbbuf, lbbuf, lbbuf );

if( selectflag )
         slut( lutsource, lutnum );
   } init_sign_extension_lut( lutsource, lutnum, selectflag )
   int lutsource, lutnum, selectflag;
   {
      unsigned int buf[ LUTSIZE ];
      unsigned char lbbuf[ LUTSIZE ];

threshscale( 0, 0, HALFSCALE, FULLSCALE, FULLSCALE, buf );
      cwb( buf, lbbuf, NULL, LUTSIZE );

wlut( lutsource, lutnum, 0, LUTSIZE, lbbuf, lbbuf, lbbuf );

if( selectflag )
         slut( lutsource, lutnum );
   } init_linear_colorscale_lut( lutsource, lutnum, selectflag )
   int lutsource, lutnum, selectflag;
   {
      unsigned int buf[ LUTSIZE ];
      unsigned char i, redbuf[ LUTSIZE ], greenbuf[ LUTSIZE ],
         bluebuf[ LUTSIZE ];

scaling( 0, 0, FULLSCALE, FULLSCALE, buf );
      cwb( buf, redbuf, NULL, LUTSIZE );

if( ! lutsource )
         invert( LUTSIZE, redbuf );

scaling( 0, 0, HALFSCALE, HALFSCALE, buf );
```

```
    scaling( HALFSCALE + 1, HALFSCALE, FULLSCALE, 0, buf );
    cwb( buf, greenbuf, NULL, LUTSIZE );

if( ! lutsource )
       invert( LUTSIZE, greenbuf );

scaling( 0, FULLSCALE, FULLSCALE, 0, buf );
    cwb( buf, bluebuf, NULL, LUTSIZE );

if( ! lutsource )
       invert( LUTSIZE, bluebuf );

redbuf[ ZERO ] = ZERO;
    greenbuf[ ZERO ] = ZERO;
    bluebuf[ ZERO ] = ZERO;

redbuf[ FULLSCALE ] = FULLSCALE;
    greenbuf[ FULLSCALE ] = FULLSCALE;
    bluebuf[ FULLSCALE ] = FULLSCALE;

wlut( lutsource, lutnum, 0, LUTSIZE, redbuf, greenbuf, bluebuf );

if( selectflag )
       slut( lutsource, lutnum );
  } init_log_grayscale_lut( lutsource, lutnum, selectflag )
   int lutsource, lutnum, selectflag;
   {
     unsigned int buf[ LUTSIZE ], x;
     double temp;
     unsigned char lbbuf[ LUTSIZE ], hbbuf[ LUTSIZE ];

scaling( 0, 0, FULLSCALE, FULLSCALE, buf );
     cwb( buf, lbbuf, NULL, LUTSIZE );
     lbbuf[ 0 ] = 2;
     lbbuf[ 1 ] = 2;

for( x = 0; x < LUTSIZE; x++ )
        {
          temp = ( lbbuf[ x ] );
          temp = log10 ( temp ) * 100;
          buf[ x ] = temp;
        } cwb( buf, lbbuf, NULL, LUTSIZE );
     lbbuf[ 0 ] = 0;
     lbbuf[ 1 ] = 15;

if( ! lutsource )
        invert( LUTSIZE, lbbuf );

wlut( lutsource, lutnum, 0, LUTSIZE, lbbuf, lbbuf, lbbuf );
     if( selectflag )
        slut( lutsource, lutnum );
   }
init_linear_overlut( lutsource, lutnum, selectflag )
   int lutsource, lutnum, selectflag;
   {
     unsigned char redbuf[ OVERLUTSIZE ], greenbuf[ OVERLUTSIZE ],
        bluebuf[ OVERLUTSIZE ], lbbuf[ LUTSIZE ];
     unsigned int buf[ LUTSIZE ], i;
```

```c
    scaling( 0, 0, FULLSCALE, FULLSCALE, buf );
    cwb( buf, lbbuf, NULL, LUTSIZE );

for( i = 0; i < OVERLUTSIZE; i++ )
      {
        redbuf[ i ] = 0;
        greenbuf[ i ] = 0;
        bluebuf[ i ] = 0;
      } for( i = 0; i < OVERLUTSIZE; i++ )
      {
        redbuf[ i ] = 0xFF;
        greenbuf[ i ] = 0xFF;
        bluebuf[ i ] = 0xFF;
      } olutlay( UPPER, redbuf, greenbuf, bluebuf,
        lbbuf, lbbuf, lbbuf );

if( selectflag )
        slut( lutsource, lutnum );
  }
/*****************************
 *                           *
 *     Graphics Functions    *
 *                           *
 *****************************/ write_frametitle( sourcebuffer, frametype, frametitleflag )
    int sourcebuffer, frametype, frametitleflag;
      {
        char temp[ 40 ] = ( ' ' );

opmode( GRAPHICS, sourcebuffer );
        drawmode( DRAW_REPLACE );

if ( frametitleflag )
          {
            setcolor ( FRAMETITLECOLOR );
          }
        else
          {
            setcolor ( BLACK );
          } setbcolor( BLACK );

move( 0, 0 );
        rrect( ( NUMXPIXELS - 1 ), ( NUMYPIXELS - 1 ) );
        move(1, 1);
        rrect( 509, 477);
        move( 0, 0);
        frect( ( NUMXPIXELS - 1 ), 17);

setcolor( 0 );

if ( frametitleflag )
          {
            setbcolor ( FRAMETITLECOLOR );
          }
        else
```

```
       {
         setbcolor ( BLACK );
       } move( 16, 16 );
    strcpy( temp, "Regional Hb Concentration: " );
    strcat( temp, filename );
    strcat( temp, ".DAT" );
    gtext( 1, 40, temp );

switch( frametype )
       {
         case 0:
           move ( 456, 16 );
           gtext( 1, 5, "[MAP]" );
           break;
         case 1:
           move ( 400, 16 );
           gtext( 1, 12, "[BACKGROUND]" );
           break;

case 2:
           move ( 440, 16 );
           gtext( 1, 7, "[DELTA]" );
           break;

case 3:
           move ( 408, 16 );
           gtext( 1, 11, "[REFERENCE]" );
           break;
       } opmode( PROCESS, sourcebuffer );
  } write_intensity_scale( sourcebuffer )
  int sourcebuffer;
    {
      unsigned int buf[ LUTSIZE ];
      unsigned char lbbuf[ LUTSIZE ];
      int rownum;

rampscale( 0, FULLSCALE, FULLSCALE,
        FULLSCALE, buf );
      cwb( buf, lbbuf, NULL, LUTSIZE );
      opmode( IO, sourcebuffer );

for( rownum = SCALESTART; rownum < SCALEEND; rownum++ )
         {
           roww( 128, rownum, ( LUTSIZE - 2 ), ( &lbbuf[ 1 ] ) );
         } opmode( GRAPHICS, sourcebuffer );
      drawmode( DRAW_REPLACE );
      setcolor( FULLSCALE );
      move( 127, ( SCALESTART - 2 ) );
      rrect( FULLSCALE, ( SCALEEND - SCALESTART + 2 ) );
      move( 127, ( SCALESTART - 1 ) );
      rrect( FULLSCALE, ( SCALEEND - SCALESTART ) );

drawmode( DRAW_OVER );
      setcolor( FULLSCALE );
```

```
setbcolor( BLACK );
move( 112, 475 );
gtext( 1, 4, "-128" );
move( 252, 475 );
gtext( 1, 1, "0" );
move( 366, 475 );
gtext( 1, 4, "+128" );
opmode( PROCESS, sourcebuffer );
} draw_grid( graphbuf )
   int graphbuf;
{
   unsigned int xpos, ypos, num;

slut( OUTPUT, LUT16 );

opmode( PROCESS, graphbuf );
   clear( graphbuf, BLACK );
   opmode( CGRAB, sourcebuffer );

drawmode( DRAW_OVER );
   setcolor( FULLSCALE );
   setbcolor( BLACK );

xpos = 0;

for( num = 0; num < 9; num++ )
     {
        move( xpos, 0 );
        line( xpos, ( NUMYPIXELS - 1 ) );
        move( (xpos + 1), 0 );
        line( (xpos + 1), ( NUMYPIXELS - 1 ) );
        xpos += 64;

if( xpos == NUMXPIXELS )
          xpos = 510 ;
     } xpos = 0;

for( num = 0; num < 32; num++ )
     {
        move( xpos, 236 );
        line( xpos, 246 );
        move( (xpos + 1), 236 );
        line( (xpos + 1), 246 );
        xpos += 16;
     } ypos = 0;

for( num = 0; num < 9; num++ )
     {
        move( 0, ypos );
        line( ( NUMXPIXELS - 1 ), ypos );
        move( 0, (ypos + 1 ));
        line( ( NUMXPIXELS - 1 ), (ypos + 1 ));
        ypos += 60;

if( ypos == NUMYPIXELS )
          ypos = 478 ;
     }
```

```
        ypos = 0;

for( num = 0; num < 32; num++ )
            {
            move( 252, ypos );
            line( 262, ypos );
            move( 252, (ypos + 1 ) );
            line( 262, (ypos + 1 ) );
            ypos += 15;
            } opmode( PROCESS, sourcebuffer );
}

/*****************************
 *                           *
 *     File I/O Functions    *
 *                           *
 *****************************/ store_data_file()
    {
        _settextcolor( BRIGHTWHITE );
        write_command( "STORE" );

clear_message();
        _outtext( "Enter filename: " );
        fflush( stdin );
        gets( filename );

if( filename[ 0 ] == '\0' || filename[ 0 ] == ' ' )
          {
            clear_message();
            return( 0 );
          }
        else
          {
            _makepath( pathname, "C", "\\IP\\LCF", filename, "DAT" );
            strcpy( filename, strupr( filename ) ) ;

if( access( pathname, 0 ) == -1 )
               {
                 opmode( IO, sourcebuffer );
                 store_data_header( sourcebuffer );
                 todisk( pathname );
                 clear_message();
                 sprintf( textbuffer, "%s.DAT  stored.", filename );
                 _outtext( textbuffer );
                 opmode( PROCESS, sourcebuffer );
               }
            else
               {
                 clear_message();
                 sprintf( textbuffer, "File already exists." );
                 _outtext( textbuffer );
               }
          }
    }
```

```c
retrieve_data_file()
    {
       _settextcolor( BRIGHTWHITE );
       write_command( "RETRIEVE" );
       clear_message();
       _outtext( "Enter filename: " );
       fflush( stdin );
       gets( filename );
       if( filename[ 0 ] == '\0' || filename[ 0 ] == ' ' )
         {
            clear_message();
            return( 0 );
         }
       else
         {
            _makepath( pathname, "C", "\\IP\\LCF", filename, "DAT" );
            strcpy( filename, strupr( filename ) );

if( access( pathname, 0 ) != -1 )
              {
                 opmode( IO, sourcebuffer );
                 fromdisk( pathname );
                 retrieve_data_header( sourcebuffer );
                 clear_message();
                 sprintf( textbuffer, "%s.DAT  retrieved.", filename );
                 _outtext( textbuffer );
                 write_filename();
                 opmode( PROCESS, sourcebuffer );
              }
            else
              {
                 clear_message();
                 sprintf( textbuffer, "File doesn't exist." );
                 _outtext( textbuffer );
              }
         }
    } store_data_header( sourcebuffer )
  int sourcebuffer;
    {
       char temp[ 8 ];

initialize_data_header();

strcpy( headerbuffer, filename );
       strcat( headerbuffer, DELIMITER );

itoa( frametype, temp, DECIMAL );
       strcat( headerbuffer, temp );
       strcat( headerbuffer, DELIMITER );

itoa( sourcebuffer, temp, DECIMAL );
       strcat( headerbuffer, temp );
       strcat( headerbuffer, DELIMITER );

itoa( overlaybuffer, temp, DECIMAL );
       strcat( headerbuffer, temp );
       strcat( headerbuffer, DELIMITER );

itoa( slopenumber, temp, DECIMAL );
       strcat( headerbuffer, temp );
       strcat( headerbuffer, DELIMITER );
```

```c
        itoa( offsetvalue, temp, DECIMAL );
        strcat( headerbuffer, temp );
        strcat( headerbuffer, DELIMITER );

itoa( gainvalue, temp, DECIMAL );
        strcat( headerbuffer, temp );
        strcat( headerbuffer, DELIMITER );

itoa( iluttype, temp, DECIMAL );
        strcat( headerbuffer, temp );
        strcat( headerbuffer, DELIMITER );

itoa( oluttype, temp, DECIMAL );
        strcat( headerbuffer, temp );
        strcat( headerbuffer, DELIMITER );

itoa( filternumber, temp, DECIMAL );
        strcat( headerbuffer, temp );
        strcat( headerbuffer, DELIMITER );

itoa( palettenumber, temp, DECIMAL );
        strcat( headerbuffer, temp );
        strcat( headerbuffer, DELIMITER );

gcvt( elapsed_time, 6, temp );
        strcat( headerbuffer, temp );
        strcat( headerbuffer, DELIMITER );

roww( 0, ( NUMYPIXELS -1 ), NUMXPIXELS, headerbuffer );
    } retrieve_data_header( sourcebuffer )
    int sourcebuffer;
    {
        initialize_data_header();
        rowr( 0, ( NUMYPIXELS -1 ), NUMXPIXELS, headerbuffer );
        clear_last_row( sourcebuffer );
        retrieve_header_fields();
    } retrieve_header_fields()
    {
        find_header_field( 0 );
        strcpy( filename, headerpointer );

find_header_field( 1 );
        frametype = atoi( headerpointer );

find_header_field( 2 );
        sourcebuffer = atoi( headerpointer );

find_header_field( 3 );
        overlaybuffer = atoi( headerpointer );

find_header_field( 4 );
        slopenumber = atoi( headerpointer );

find_header_field( 5 );
        offsetvalue = atoi( headerpointer );
```

```
        find_header_field( 6 );
        gainvalue = atoi( headerpointer );

find_header_field( 7 );
        iluttype = atoi( headerpointer );

find_header_field( 8 );
        oluttype = atoi( headerpointer );

find_header_field( 9 );
        filternumber = atoi( headerpointer );

find_header_field( 10 );
        palettenumber = atoi( headerpointer );

find_header_field( 11 );
        elapsed_time = atof( headerpointer );
    } find_header_field( fieldnumber )
  int fieldnumber;
    {
        char copybuffer[ NUMXPIXELS ];

strcpy( copybuffer, headerbuffer );
        headerpointer = copybuffer;

headerpointer = strtok( copybuffer, DELIMITER );

if ( fieldnumber )
          {
                while( ( *headerpointer != '\0' ) && ( fieldnumber ) )
                  {
                     headerpointer = strtok( NULL, DELIMITER );
                     fieldnumber--;
                  }

}
    } initialize_data_header()
    {
        int i;

headerpointer = headerbuffer;

for( i = 0; i <= ( NUMXPIXELS - 1 ); i++ )
            *headerpointer++ = '\0' ;
    }

/***********************
 *                     *
 *   Menu Functions    *
 *                     *
 ***********************/ init_vga_screen()
    {
        int mode = _VRES16COLOR;
```

```c
    oldcolor = _gettextcolor();

while( !_setvideomode( mode ) )
      mode--;

if( mode == _TEXTMONO )
      return( 0 );

printf( "\033[37m" );
    _clearscreen( _GWINDOW );
    _settextcursor( CURSOROFF );
    _wrapon( _GWRAPOFF ) ;

set_vtitle_window();
    _settextcolor( BRIGHTWHITE );
    _settextposition( 1, 28 );
    _outtext( "REGIONAL Hb CONCENTRATION" );

set_data_window();

set_menu_window();
    _settextcolor( BRIGHTWHITE );
    print_line();

_settextposition( 3, 1 );
    _outtext( "F1> Reference " );

_settextposition( 3, 17 );
    _outtext( "F2> Map        " );

_settextposition( 3, 33 );
    _outtext( "F3> Store      " );

_settextposition( 3, 49 );
    _outtext( "F4> Retrieve  " );

_settextposition( 3, 65 );
    _outtext( "F5> Threshold " );

_settextposition( 4, 1 );
    _outtext( "F6> Autoscale " );

_settextposition( 4, 17);
    _outtext( "F7> Average    " );

_settextposition( 4, 33 );
    _outtext( "F8> Focus      " );

_settextposition( 4, 49 );
    _outtext( "F9> Display    " );

_settextposition( 4, 65 );
    _outtext( "F10> Quit      " );

_settextposition( 3, 1 );
} wait_for_start_key( keynumber )
  int keynumber;
    {
      set_menu_window();
```

```
        clear_message();
        _settextcolor( BRIGHTWHITE );
        _outtext( "Press any key to acquire frame... " );
        _settextcolor( BRIGHTWHITE );
        inputkey.i = _bios_keybrd( 0 );
        clear_message();
    } wait_for_end_key()
    {
        set_menu_window();
        clear_message();
        _settextcolor( BRIGHTWHITE );
        _outtext( "Press any key to end acquisition... " );
        _settextcolor( BRIGHTWHITE );
        inputkey.i = _bios_keybrd( 0 );
        clear_message();
        _settextcolor( BRIGHTWHITE );
        _outtext( "Acquisition ended. " );
        _settextcolor( BRIGHTWHITE );
    } confirm_acquisition()
    {
        clear_message();
        _settextcolor( BRIGHTWHITE );
        _outtext( "Frame acquired. " );
        _settextcolor( BRIGHTWHITE );
    } confirm_computation()
    {
        clear_message();
        _settextcolor( BRIGHTWHITE );
        _outtext( "Frame computed. " );
        _settextcolor( BRIGHTWHITE );
    } write_command(commandstring)
    char commandstring[ 10 ];
    {
        int colnum;

set_menu_window();
        _settextposition( COMMAND_ROW, COMMAND_COL );

for( colnum = COMMAND_COL; colnum < MESSAGE_COL; colnum ++ )
            _outtext( " " );

_settextposition( COMMAND_ROW, COMMAND_COL );
        _settextcolor( BRIGHTWHITE );
        _outtext( commandstring );
        _settextcolor( BRIGHTWHITE );
        _settextposition( COMMAND_ROW, COMMAND_COL );
    }
```

```c
write_message( textbuffer )
  char textbuffer[ LASTCOL ];
    {
       int colnum;

set_menu_window();
       _settextposition( MESSAGE_ROW, MESSAGE_COL );

for( colnum = MESSAGE_COL; colnum < LASTCOL; colnum ++ )
         _outtext( " " );

_settextposition( MESSAGE_ROW, MESSAGE_COL );
       _settextcolor( BRIGHTWHITE );
       _outtext( textbuffer );
       _settextcolor( BRIGHTWHITE );
       _settextposition( MESSAGE_ROW, MESSAGE_COL );
    } print_line()
    {
       int colnum;

set_menu_window();
       _settextposition( 1, 1 );

for( colnum = 1; colnum < LASTCOL; colnum ++ )
          _outtext( "\x0C4" );

_settextposition( COMMAND_ROW, COMMAND_COL );
    } clear_message()
    {
       int colnum;

set_menu_window();
       _settextposition( MESSAGE_ROW, MESSAGE_COL );

for( colnum = MESSAGE_COL; colnum < LASTCOL; colnum ++ )
         _outtext( " " );

_settextposition( MESSAGE_ROW, MESSAGE_COL );
    } set_vtitle_window()
    {
       _settextwindow( VTITLE_T_ROW, VTITLE_L_COL,
                       VTITLE_B_ROW, VTITLE_R_COL );
    } set_menu_window()
    {
       _settextwindow( MENU_T_ROW, MENU_L_COL,
                       MENU_B_ROW, MENU_R_COL );
    }
```

```c
/*************************************
 *                                   *
 *      Data Display Functions       *
 *                                   *
 *************************************/ write_data_values( frametype )
    int frametype;
    {
        write_filename();
        write_log_slope();
        write_input_lut();
        write_output_lut();
        write_intensity_min( frametype );
        write_intensity_max( frametype );
        write_intensity_mode( frametype );
        write_intensity_at( frametype, histindex );
    } write_filename()
    {
        set_data_window();
        clear_data( 1 );
        _settextposition( 1, 1 );
        sprintf( textbuffer, "File name:     %s.DAT", filename );
        _outtext( textbuffer );
    } get_reference_time()
    {
        timeflag = 1;
        time( &start );
    } write_current_time()
    {
        time( &current_time );
        elapsed_time = difftime( current_time, start );

set_data_window();
        clear_data( 3 );
        _settextposition( 3, 1 );
        sprintf( textbuffer, "Current time: %6.1f sec.", elapsed_time );
        _outtext( textbuffer );
    } write_frame_time()
    {
        time( &current_time );
        elapsed_time = difftime( current_time, start );

set_data_window();
        clear_data( 4 );
        _settextposition( 4, 1 );
        sprintf( textbuffer, "Frame time:   %6.1f sec.", elapsed_time );
        _outtext( textbuffer );
    }
```

```
write_blank_frame_time()
    {
       set_data_window();
       clear_data( 4 );
       _settextposition( 4, 16 );
       sprintf( textbuffer, "    " );
       _outtext( textbuffer );
    } write_log_slope()
    {
       set_data_window();
       clear_data( 6 );
       _settextposition( 6, 1 );
       sprintf( textbuffer, "Log slope:      %d", slopenumber );
       _outtext( textbuffer );
    } write_input_lut()
    {
       int i = 1;

set_data_window();
       clear_data( 9 );
       _settextposition( 9, 1 );
       sprintf( textbuffer, "Input LUT:      %d ", i );
       _outtext( textbuffer );
    } write_output_lut()
    {
       int i = 1;

set_data_window();
       clear_data( 10 );
       _settextposition( 10, 1 );
       sprintf( textbuffer, "Output LUT:     %d ", i );
       _outtext( textbuffer );
    } write_intensity_min( frametype )
  int frametype;
    {
       int i;
       float min;
       i = 0;

while( histvalue[ frametype ] [ i ] < yminvalue[ frametype] ) i++;
       min = histvalue[ frametype ] [ i ];
       set_data_window();
       clear_data( 12 );
       _settextposition( 12, 1 );
       sprintf( textbuffer, "Intensity min:  [%3d]  %6.2f %% ", i, min );
       _outtext( textbuffer );
    }
```

```
write_intensity_max( frametype )
  int frametype;
    {
      int i;
      float max;

i = ( HISTSIZE_8 - 1 );

while( histvalue[ frametype ] [ i ] < yminvalue[ frametype] ) i--;

max = histvalue[ frametype ] [ i ];

set_data_window();
      clear_data( 13 );
      _settextposition( 13, 1 );
      sprintf( textbuffer, "           max: [%3d]   %6.2f %%   ", i, max );
      _outtext( textbuffer );
    } write_intensity_mode( frametype )
  int frametype;
    {
      int i, ipointer;
      float mode;

mode = 0;

for( i = 0; i < HISTSIZE_8; i++ )
        {
          if( histvalue[ frametype ] [ i ] >= mode )
            {
              mode = histvalue[ frametype ] [ i ];
              ipointer = i;
            }
        } set_data_window();
      clear_data( 14 );
      _settextposition( 14, 1 );
      sprintf( textbuffer, "           mode: [%3d]   %6.2f %%   ",
                                          ipointer, mode);
      _outtext( textbuffer );
    } write_intensity_at( frametype, histindex )
  int frametype, histindex;
    {
      float indexvalue;

indexvalue = histvalue[ frametype] [ histindex ];

set_data_window();
      clear_data( 17 );
      _settextposition( 17, 1 );
      sprintf( textbuffer, "Cursor value:   [%3d]   %6.2f %%   ",
                           histindex, indexvalue );
      _outtext( textbuffer );
    }
```

```c
set_data_window()
    {
        _settextwindow( DATA_T_ROW, DATA_L_COL,
                        DATA_B_ROW, DATA_R_COL );
    } clear_data( datarow )
  int datarow;
    {
        _settextposition( datarow, 15 );
        sprintf( textbuffer, "                " );
        _outtext( textbuffer );
    }

/******************************
*                             *
*      Histogram Functions    *
*                             *
******************************/ compute_histogram( frametype )
  int frametype;
    {
      int i;
      float temp;

histo( frametype, histbuf );
      ymaxvalue[ frametype ] = histbuf[ 1 ] / ( ( 512.0 * 480.0 ) / 100.0 );
      yminvalue[ frametype ] = ymaxvalue[ frametype ] / 5000.0;

for( i = 0; i < HISTSIZE_8; i++ )
        {
          temp = histbuf[ ( i + 2 ) ];
          histvalue[ frametype ] [ i ] = temp / ( ( 512.0 * 480.0 ) / 100.0 );
        } for( i = 0; i < HISTSIZE_8; i++ )
        intenvalue[ i ] = i ;
    } display_histogram( histflag, frametype )
  int histflag, frametype;
    {
      int i;

_setviewport( 0, 50, 320, 380);
      _clearscreen (_GVIEWPORT);
      _setviewport( 0, 0, 320, 479 );
      initialize_histogram( frametype);

if( histflag )
        {
          env.chartwindow.x1 = HISTO1_WINDOW_X1;
          env.chartwindow.x2 = HISTO1_WINDOW_X2;
          strcpy( env.xaxis.scaletitle.title, "intensity" );
          strcpy( env.yaxis.scaletitle.title, "%" );

switch( frametype )
            {
```

```
            case MAP:
              strcpy( env.subtitle.title,
                       "         FRAME HISTOGRAM: MAP" );
              break;

case BACKGROUND:
              strcpy( env.subtitle.title,
                       "         FRAME HISTOGRAM: BACKGROUND" );
              break;

case DELTA:
              strcpy( env.subtitle.title,
                       "         FRAME HISTOGRAM: DELTA" );
              break;

case REFERENCE:
              strcpy( env.subtitle.title,
                       "         FRAME HISTOGRAM: REFERENCE" );
              break;
            } if ( ymaxvalue[ frametype ] < 10.0 )
            env.yaxis.ticdecimals = 2;
          else
            env.yaxis.ticdecimals = 1;

_pg_chartscatter( &env, intenvalue, histvalue[ frametype],
            HISTSIZE_8 );

if( ymaxvalue[ frametype ] >= 99.95 )
            _setviewport( 81, 75, 294, 338 );
          else
            _setviewport( 72, 75, 295, 338 );

_setwindow( TRUE, 0.0, 0.0, HISTSIZE_8, ymaxvalue[ frametype ] );

for( i = 0; i < 256; i++ )
            {
              _moveto_w( i, 0.0 );
              _lineto_w( i, histvalue[ frametype ] [ i ] );
            }

}

} initialize_histogram( frametype )
  int frametype;
    {
      _pg_initchart();
      _pg_defaultchart( &env, _PG_SCATTERCHART, _PG_POINTANDLINE );

env.subtitle.justify= _PG_CENTER;

env.chartwindow.border = FALSE;
      env.chartwindow.y1 = HISTO_WINDOW_Y1;
      env.chartwindow.y2 = HISTO_WINDOW_Y2;

_pg_getpalette( pal);
      pal[1].plotchar = ' ';
      _pg_setpalette( pal );
```

```
    env.xaxis.grid = FALSE;
    env.xaxis.gridstyle = 1;
    env.xaxis.labeled = TRUE;
    env.xaxis.autoscale = FALSE;
    env.xaxis.scalemin = 0;
    env.xaxis.scalemax = FULLSCALE + 1;
    env.xaxis.ticinterval = ( FULLSCALE + 1 ) / 4;
    env.xaxis.ticdecimals = 0;

env.yaxis.grid = TRUE;
    env.yaxis.gridstyle = 13;
    env.yaxis.labeled = TRUE;
    env.yaxis.autoscale = FALSE;
    env.yaxis.scalemin = 0;
    env.yaxis.scalemax = ymaxvalue[ frametype ];
    env.yaxis.ticinterval = ymaxvalue[ frametype ] / 6.0;
    env.yaxis.ticdecimals = 0;
}

/***********************************************
 *                                             *
 *                                             *
 *       Test and Temporary Functions          *
 *                                             *
 ***********************************************/ test_overlay()
    {
    int i;

video_off();
    slut( OUTPUT, LUT16 );

clear( FB2, BLACK );
    outpath( FB0, MINUSVALUE, FB2, MSB );
    outpath( FB0, MINUSVALUE, FB2, MSB );
    snapshot( 0 );

opmode( GRAPHICS, FB2 );
    move( NUMXPIXELS / 2, NUMYPIXELS / 2 );

for ( i = 16; i < 256; i += 16 )
        {
        setcolor( i );
        circle( ( i / 16 ) * 15 );
        } opmode( PROCESS, sourcebuffer );
    video_on();
    } test_ports()
    {
    int testflag = 1;

while( testflag )
        {
        trigger_flash( 0 );
        toggle_log_slope();
        select_filter( NM_586 );
        select_filter( NM_569 );
        }
    }
```

I claim:

1. A system for determining anatomical localization of functional activity of a human brain during a neurosurgical procedure comprising:
   a) illumination means for generating an illuminating light;
   b) optical bandpass filter means disposed between the illumination means and the brain for enabling sequential illumination of an exposed surface of the brain with predetermined wavelengths of monochromatic light;
   c) a video camera generating a video signal representing an image of the illuminated exposed surface of the brain;
   d) video processing means coupled to the video camera for converting the generated video signal to a log signal which directly represents reflectance of said exposed brain surface;
   e) image processing means coupled to said video processing means for digitizing and analyzing said log signal and for computing regional total hemoglobin concentration of said exposed brain surface;
   f) display means coupled to said image processing means for displaying an image representing the computed regional total hemoglobin concentration of said exposed brain surface.

2. The system defined by claim 1 further comprising stimulation signal generation means for generating at least one of a tactile, an auditory and a visual signal for stimulating predetermined sensory pathways of a human being undergoing said neurosurgical procedure.

3. The system defined by claim 2 wherein said stimulation signal generation means comprises at least one of a tactile signal generation device, an audio signal generation device and a visual signal generation device coupled to a computer for generating said tactile, audio and visual signals under control of said computer.

4. The system defined by claim 1 wherein the brain is stimulated by performance of a predetermined neuropsychological task by a human being undergoing said neurosurgical procedure.

5. The system defined by claim 1 wherein said illumination means comprises:
   a) an electronic flash unit coupled to a computer for generating the illuminating light under control of the computer; and
   b) a collimator lens assembly coupled to said electronic flash unit for collimating the illuminating light.

6. The system defined by claim 1 wherein said optical bandpass filter means comprises:
   a) a filter wheel having two filter apertures, said filter wheel adapted to retain two thin-film interference filters; and
   b) two thin-film interference filters mounted on said filter wheel, said two thin-film interference filters having bandpass centers at 569.0 nm. and 586.0 nm. respectively, with 50% transmission bandwidths of 1.8 nm., and with 10% transmission bandwidths of 2.6 nm.;
   c) a filter positioner coupled to said filter wheel and a computer for interposing one of said two filters between said illuminating means and said brain under control of said computer.

7. The system defined by claim 1 wherein said video camera comprises a high-resolution charge-coupled device interline-transfer video camera.

8. The system defined by claim 1 wherein said video processing means comprises:
   a) means for transforming the video signal generated by said camera into a logarithmic signal proportional to the $\log_{10}$ of the absolute value of the video signal; and
   b) multiplexer means coupled to said transforming means, a reference voltage source, and said video camera through means for inverting and DC-restoring the video signal generated by said video camera, said multiplexer means for selecting one of said logarithmic signal, said inverted and DC-restored video signal, and said reference voltage, and passing said selected signal to said image processing means.

9. The system defined by claim 1 wherein said image processing means comprises:
   a) analog-to-digital converter means coupled to said video processing means for digitizing video information generated by said video processing means;
   b) memory means coupled to said analog-to-digital converter means for storing at least four video frames of digitized video information;
   c) arithmetic processor means coupled to said memory means for performing predetermined arithmetic operations on said digitized video information; and
   d) digital-to-analog converter means coupled to said memory means for generating RGB video signals from said arithmetically processed digitized video information.

10. The system defined by claim 1 wherein said display means comprises an RGB monitor coupled to said image processing means.

11. A method for determining anatomical localization of functional activity of a human brain during a neurosurgical procedure comprising the steps of:
    a) sequentially illuminating an exposed surface of the brain with predetermined wavelengths of monochromatic light;
    c) generating a video signal representing an image of the illuminated exposed surface of the brain;
    d) converting the generated video signal to a log signal which directly represents reflectance of said exposed brain surface;
    e) selecting one of said log signal, said video signal after inverting and DC-restoring the video signal, and a reference voltage;
    f) computing regional total hemoglobin concentration of said exposed brain surface using said selected signal; and
    g) displaying an image representing the computed regional total hemoglobin concentration of said exposed brain surface.

12. The method defined by claim 11 further comprising the step of generating a signal for stimulating predetermined sensory pathways of said human being.

13. The system defined by claim 12 wherein said stimulation signal generating step comprises the step of generating at least one of a tactile signal, an audio signal, and a visual signal.

14. The method defined by claim 11 further comprising the step of stimulating the brain by performance of a predetermined neuropsychological task.

15. The method defined by claim 11 wherein said sequentially illuminating step comprises the steps of:
   a) generating the illuminating light using an electronic flash unit controlled by a computer;
   b) collimating the illuminating light; and
   c) passing the collimated illuminating light through two thin-film interference filters having bandpass centers at 569.0 nm and 586.0 nm respectively, with 50% transmission bandwidths of 1.8 nm, and with 10% transmission bandwidths of 2.6 nm, wherein a filter positioner is used for interposing one of said two filters between said electronic flash unit and said brain under control of said computer.

16. The method defined by claim 11 wherein said video signal is generated by a high-resolution charge-coupled device interline-transfer video camera.

17. The method defined by claim 11 wherein said converting step comprises the step of transforming the video signal into a logarithmic signal proportional to the $\log_{10}$ of the absolute value of the video signal.

18. The method defined by claim 11 wherein said computing step comprises steps of:
   a) digitizing video information generated by said video processor means;
   b) storing at least four video frames of said digitized video information;
   c) performing predetermined arithmetic operations on said digitized video information; and
   d) generating RGB video signals from said arithmetically processed digitized video information.

* * * * *